(12) United States Patent
Zbozien

(10) Patent No.: US 10,994,047 B2
(45) Date of Patent: May 4, 2021

(54) PEPTIDE DENDRIMERS COMPRISING FIBRINOGEN-BINDING PEPTIDES

(71) Applicant: HAEMOSTATIX LIMITED, Nottingham (GB)

(72) Inventor: Renata Zbozien, Nottingham (GB)

(73) Assignee: HAEMOSTATIX LIMITED, Nottingham (GB)

( * ) Notice: Subject to any disclaimer, the term of this patent is extended or adjusted under 35 U.S.C. 154(b) by 0 days.

(21) Appl. No.: 15/110,630

(22) PCT Filed: Jan. 8, 2015

(86) PCT No.: PCT/GB2015/050024
§ 371 (c)(1),
(2) Date: Jul. 8, 2016

(87) PCT Pub. No.: WO2015/104544
PCT Pub. Date: Jul. 16, 2015

(65) Prior Publication Data
US 2016/0324977 A1 Nov. 10, 2016

(30) Foreign Application Priority Data
Jan. 8, 2014 (GB) .................................. 1400292

(51) Int. Cl.
| | |
|---|---|
| *A61K 38/36* | (2006.01) |
| *A61L 26/00* | (2006.01) |
| *A61K 47/64* | (2017.01) |
| *A61K 41/17* | (2020.01) |
| *A61K 47/42* | (2017.01) |

(52) U.S. Cl.
CPC .......... *A61L 26/008* (2013.01); *A61K 38/363* (2013.01); *A61K 41/17* (2020.01); *A61K 47/42* (2013.01); *A61K 47/641* (2017.08); *A61L 26/0028* (2013.01); *A61L 26/0052* (2013.01); *A61L 26/0066* (2013.01); *A61L 2300/252* (2013.01); *A61L 2300/418* (2013.01); *A61L 2400/04* (2013.01)

(58) Field of Classification Search
None
See application file for complete search history.

(56) References Cited

U.S. PATENT DOCUMENTS

| | | |
|---|---|---|
| 2003/0171539 A1 | 9/2003 | Quentin et al. |
| 2004/0214272 A1* | 10/2004 | La Rosa ............... C07K 14/415 435/69.1 |
| 2005/0123588 A1 | 6/2005 | Zhu et al. |
| 2006/0104970 A1 | 5/2006 | Margel et al. |
| 2012/0114682 A1* | 5/2012 | Barker ................. C07K 5/1008 424/185.1 |
| 2013/0310853 A1 | 11/2013 | Zaugg et al. |

FOREIGN PATENT DOCUMENTS

| | | |
|---|---|---|
| WO | 97/49731 A1 | 12/1977 |
| WO | 96/17633 A1 | 6/1996 |
| WO | 96/20216 A1 | 7/1996 |
| WO | 0226779 A2 | 4/2002 |
| WO | 2006/012541 A2 | 2/2006 |
| WO | 2007/015107 A2 | 2/2007 |

(Continued)

OTHER PUBLICATIONS

Laudano et al. ('Synthetic peptide derivatives that bind to fibrinogen and prevent the polymerization of fibrin monomers' Proc Natl Acad Sci USA v75(7) Jul. 1978 pp. 3085-3089) (Year: 1978).*
La Rosa Seq ID No. 201985 (retrieved from http://seqdata.uspto.gov/?pageRequest=viewSequence&DocID=20040214272&seqID=201985 on Apr. 13, 2020, 2 pages) (Year: 2020).*
Yu et al. ('Sequential conjugation of 6-aminohexanoic acids and L-arginines to poly(amidoamine) dendrimer to modify hydrophobicity and flexibility of the polymeric gene carrier' Bull. Korean Chem. Soc. v32(2) 2011 pp. 651-655) (Year: 2011).*
International Search Report and Written Opinion for corresponding Application No. PCT/GB2015/050024 (Apr. 24, 2015).
Miekka et al., "Inactivation of Viral and Prion Pathogens by Gamma-Irradiation Under Conditions that Maintain the Integrity of Human Albumin," Vox Sanguinis 84(1):36-44 (2003).

(Continued)

*Primary Examiner* — Ronald T Niebauer
(74) *Attorney, Agent, or Firm* — Troutman Pepper Hamilton Sanders LLP (Rochester)

(57) ABSTRACT

Peptide dendrimers and agents are described, which can be used for polymerising fibrinogen and as haemostatic agents. The peptide dendrimers comprise a branched core, and a plurality of fibrinogen-binding peptides separately covalently attached to the branched core. The branched core comprises: i) from two to ten multi-functional amino acid residues, wherein each fibrinogen-binding peptide is separately covalently attached to a multi-functional amino acid residue of the branched core; il) a plurality of multi-functional amino acid residues, wherein one or more fibrinogen-binding peptides are separately covalently attached to each of at least two adjacent multi-functional amino acid residues of the branched core; Hi) a plurality of multi-functional amino acid residues, wherein two or more fibrinogen-binding peptides are separately covalently attached to at least one of the multi-functional amino acid residues of the branched core; iv) a plurality of multi-functional amino acid residues, wherein two or more multi-functional amino acid residues are covalently linked through a side chain of an adjacent multi-functional amino acid residue; or y) a single multi-functional amino acid residue, and a fibrinogen-binding peptide is separately covalently attached to each functional group of the multi-functional amino acid residue, The. multi-functional amino acid residues comprise tri- or tetra-functional amino acid residues, or tri- and tetra-functional amino acid residues, or the single multi-functional amino acid residue is a tri- or tetra-functional amino acid residue.

25 Claims, 7 Drawing Sheets
Specification includes a Sequence Listing.

(56) References Cited

FOREIGN PATENT DOCUMENTS

| WO | 2008/065388 A2 | | 6/2008 |
|---|---|---|---|
| WO | 2010/088469 A2 | | 8/2010 |
| WO | WO2012/104638 | * | 8/2012 |
| WO | 2013/053769 A1 | | 4/2013 |
| WO | 2013/114132 A1 | | 8/2013 |

OTHER PUBLICATIONS

Sadler et al., "Peptide Dendrimers: Applications and Synthesis," J. Biotechnol. 90(3):195-229 (2002).
Elvin et al., "The development of Photochemically Crosslinked Native Fibrinogen as a Rapidly Formed and Mechanically Strong Surgical Tissue Sealant," Biomaterials 30(11):2059-2065 (2009).
Haynie et al., "Antimicrobial Activities of Amphiphilic Peptides Covalently Bonded to a Water-Insoluble Resin," Antimicrob. Agents Chemother. 39(2):301-307 (1995).
Tomalia et al., "Discovery of Dendrimers and Dendritic Polymers: A Brief Historical Perspective," J. Polymer Sci. 40:2719-28 (2002).

* cited by examiner

US 10,994,047 B2

PEPTIDE DENDRIMERS COMPRISING FIBRINOGEN-BINDING PEPTIDES

This application is a national stage application under 35 U.S.C. § 371 of PCT Application No. PCT/GB2015/050004, filed Jan. 8, 2015, which claims the priority benefit of Great Britain Application No. 1400292.7, filed Jan. 8, 2014, which are hereby incorporated by reference in their entirety.

This invention relates to peptide dendrimers and agents comprising fibrinogen-binding peptides, to compositions comprising the peptide dendrimers or agents, and to their use for polymerising fibrinogen and as haemostatic agents.

Formation of insoluble fibrin polymer from its soluble precursor fibrinogen is the final stage of blood clotting. Conversion of fibrinogen to fibrin occurs in three steps: limited proteolysis of fibrinogen to fibrin monomer by thrombin; assembly of fibrin monomers into half-staggered, double-stranded protofibrils; and cross-linking of assembled fibrin to strengthen the clot.

The fibrinogen molecule consists of three pairs of non-identical polypeptide chains, Aα, Bβ and γ, linked together by disulfide bonds. Fibrinogen chains are folded into three distinct structural regions, two distal D regions linked to one central E region. Each D region contains polymerization 'a' and 'b' holes located in the C terminus of the γ and Bβ chains, respectively. Thrombin catalyses the removal of short peptides, fibrinopeptides A (FpA) and B (FpB), from the amino-terminus of the Aα and Bβ chains of fibrinogen in the central E region, respectively, exposing two polymerisation sites: "knob A", with amino-terminal sequence Gly-Pro-Arg-; and "knob B", with amino-terminal sequence Gly-His-Arg-. The newly exposed polymerization knobs of one fibrin monomer interact with corresponding holes of another fibrin monomer through 'A-a' and 'B-b' knob-hole interactions, resulting in the assembly of fibrin monomers into half-staggered, double-stranded protofibrils.

The protofibrils aggregate laterally to make thicker fibres that coalesce to form a three-dimensional network of fibrin clot. FpA is cleaved from fibrinogen more rapidly than FpB. Removal of FpA triggers formation of protofibrils, while removal of FpB coincides with their lateral aggregation. FpB release, which is very slow at the start of the reaction, is accelerated upon polymer formation. This delay in FpB cleavage is necessary for normal fibrin assembly, and is also connected with the formation of different types of clots. Fibrin I, in which only the FpAs are removed, is less compact and is more readily digested by plasmin, whereas fibrin II, in which both FpA and FpB are removed, is more compact and more resistant to fibrinolysis.

Studies with snake venom enzymes that remove only FpA or principally FpB have demonstrated that fibrin clots can be formed by either 'A-a' or 'B-b' interactions, indicating that both interactions can mediate protofibril formation. Experiments with a variant recombinant fibrinogen showed that 'B-b' interactions may play a substantial role in protofibril formation when 'A-a' interactions are weakened. Other studies have demonstrated that only 'A-a' interactions occur during the binding of fibrin fragments to fibrinogen molecules even when both 'B' knobs and 'b' holes are available, and that 'B-b' knob-hole interactions were apparent only when 'A-a' interactions were excluded. However, peptide inhibition studies have indicated that 'B-b' interactions can occur simultaneously with 'A-a'.

Fibrin is stabilised by the formation of covalent cross-links between the side chains of different molecules in the fibrin fibre. Peptide bonds are formed between specific glutamine and lysine side chains in a transamidation reaction that is catalysed by Factor XIIIa.

Fibrin tissue adhesive (FTA) is the name given to products formed by mimicking the last step of the coagulation cascade to form a fibrin clot. Commercially available FTA kits rapidly produce strong, biodegradable gels that are used for haemostasis, drug delivery, and as surgical glues, and tissue sealants. Fibrinogen, Factor XIII, thrombin, and calcium ions are typically delivered via a syringe device that separates fibrinogen and Factor XIII from calcium ions and thrombin during storage. Mixing of the components during discharge from the syringe results in thrombinolysis of fibrinogen to create fibrin, which self-assembles into a gel that is later cross-linked by calcium ion-activated Factor XIII.

Conventional FTAs have the disadvantage that they are not supplied in a ready-to-use form, so the components of the FTA must be mixed before application to a wound. Once the components are mixed, the FTA must be used within a short period of time. The requirement to prepare the mixture shortly before use can be particularly disadvantageous, for example, if the product is required in an emergency.

Many FTAs utilise bovine thrombin, which is contaminated with bovine antigen, in particular bovine Factor V. Antibodies generated against this antigen can cross-react with human factor V and lead to life-threatening bleeding and, in some circumstances, anaphylaxis and death. Human thrombin has been isolated from pooled plasma of donors in an effort to minimize these risks, but has the potential to transmit blood-borne pathogens, especially viruses. A recombinant human thrombin has been developed and approved for use by the US Food and Drug Administration (FDA). It has the advantage of being minimally antigenic and does not carry the risk of viral transmission. However, it is made using a genetically modified Chinese hamster ovary cell line, and so is relatively expensive to produce.

Purified bovine, and recombinant human thrombin preparations are stored at room temperature as a powder which must be reconstituted with saline into solution before use. The FDA-approved purified human thrombin is packaged as a solution, but this can only be stored at room temperature for up to 24 hours; long-term storage requires freezing (Lew and Weaver, Biologics: Targets & Therapy 2008:2(4) 593-599). A further disadvantage of using thrombin is that it takes time for the enzyme to convert fibrinogen to fibrin, so there is a delay before blood coagulation is accelerated.

Conventional FTAs also use very high amounts of fibrinogen. Other haemostats rely on the patient's own fibrinogen for promotion of clot formation. A haemostatic matrix, termed "FLOSEAL", consists of a mixture of bovine-derived gelatin matrix, human derived thrombin, and calcium chloride. The thrombin is provided in freeze-dried form, and must be dissolved in calcium chloride solution, then mixed with the gelatin matrix, prior to use. The product must be used within eight hours of preparation. Again the requirement to prepare the mixture shortly before use may be particularly disadvantageous, for example, if the product is required in an emergency.

WO 2008/065388 describes formation of a biogel using an agent that is able to polymerise fibrinogen in the absence of thrombin. The agent comprises several fibrinogen-binding peptides conjugated to a soluble human serum albumin (HSA) carrier using the cross-linking agent succinimidyl-4-(N-maleimidomethyl)cyclohexane-1-carboxylate (SMCC). US 2012/0114682 describes use of conjugates of fibrin knob peptides to form fibrin polymers, and their use in wound repair. This document also describes the production of a conjugate comprising the fibrinogen-binding peptide GPRP (SEQ ID NO: 1) attached to polyethylene glycol (PEG). The "knob-PEG" conjugate was made by reacting a maleimide-activated PEG with a C-terminal cysteine of the synthesised knob peptide.

Conjugation methods are often complex, requiring multiple steps, some of which may need to be completed at different locations, and often result in relatively low yield of the desired product. A further disadvantage of conjugated products is that they may be sensitive to sterilising radiation, due to the carrier and/or linker materials used in their synthesis.

There is a need, therefore, to provide haemostats that can rapidly polymerise fibrinogen, can readily be produced without use of immunogenic reagents, are resistant to sterilising radiation, and can be provided in ready-to-use form.

According to a first aspect of the invention there is provided a peptide dendrimer that comprises a branched core, and a plurality of fibrinogen-binding peptides separately covalently attached to the branched core, wherein the branched core comprises:

from two to ten multi-functional amino acid residues, wherein each fibrinogen-binding peptide is separately covalently attached to a multi-functional amino acid residue of the branched core;

a plurality of multi-functional amino acid residues, wherein one or more fibrinogen-binding peptides are separately covalently attached to each of at least two adjacent multi-functional amino acid residues of the branched core;

a plurality of multi-functional amino acid residues, wherein two or more fibrinogen-binding peptides are separately covalently attached to at least one of the multi-functional amino acid residues of the branched core;

a plurality of multi-functional amino acid residues, wherein two or more multi-functional amino acid residues are covalently linked through a side chain of an adjacent multi-functional amino acid residue; or a single multi-functional amino acid residue, and a fibrinogen-binding peptide is separately covalently attached to each functional group of the multi-functional amino acid residue;

wherein the multi-functional amino acid residues comprise tri- or tetra-functional amino acid residues, or tri- and tetra-functional amino acid residues, or the single multi-functional amino acid residue is a tri- or tetra-functional amino acid residue.

Each fibrinogen-binding peptide has a different point of attachment to the branched core, so the fibrinogen-binding peptides are referred to herein as being "separately covalently attached" to the branched core.

The branched core comprises any suitable amino acid sequence. The branched core may comprise up to ten multi-functional amino acid residues, for example two to ten, or two to six multi-functional amino acid residues.

The branched core may comprise a plurality of consecutive multi-functional amino acid residues. The branched core may comprise up to ten consecutive multi-functional amino acid residues.

The term "tri-functional amino acid" is used herein to refer to any organic compound with a first functional group that is an amine (—NH$_2$), a second functional group that is a carboxylic acid (—COOH), and a third functional group. The term "tetra-functional amino acid" is used herein to refer to any organic compound with a first functional group that is an amine (—NH$_2$), a second functional group that is a carboxylic acid (—COOH), a third functional group, and a fourth functional group. The third and fourth functional group may be any functional group that is capable of reaction with a carboxy-terminal end of a fibrinogen-binding peptide, or with a functional group of a linker attached to the carboxy-terminal end of a fibrinogen-binding peptide.

Multifunctional amino acids may comprise a central carbon atom (α- or 2-) bearing an amino group, a carboxyl group, and a side chain bearing a further functional group (thereby providing a tri-functional amino acid), or a further two functional groups (thereby providing a tetra-functional amino acid.

The, or each, multi-functional amino acid residue may be a residue of a proteinogenic or non-proteinogenic multi-functional amino acid, or a residue of a natural or unnatural multi-functional amino acid.

Proteinogenic tri-functional amino acids possess a central carbon atom (α- or 2-) bearing an amino group, a carboxyl group, a side chain and an α-hydrogen levo conformation. Examples of suitable tri-functional proteinogenic amino acids include L-lysine, L-arginine, L-aspartic acid, L-glutamic acid, L-asparagine, L-glutamine, and L-cysteine.

Examples of suitable tri-functional non-proteinogenic amino acid residues include D-lysine, beta-Lysine, L-ornithine, D-ornithine, and D-arginine residues.

Thus, examples of suitable tri-functional amino acid residues for use in a peptide dendrimer of the invention include lysine, ornithine, arginine, aspartic acid, glutamic acid, asparagine, glutamine, and cysteine residues, such as L-lysine, D-lysine, beta-Lysine, L-ornithine, D-ornithine, L-arginine, D-arginine, L-aspartic acid, D-aspartic acid, L-glutamic acid, D-glutamic acid, L-asparagine, D-asparagine, L-glutamine, D-glutamine, L-cysteine, and D-cysteine residues.

Examples of suitable multi-functional unnatural amino acids suitable for use in a peptide dendrimer of the invention include Citrulline, 2,4-diaminoisobutyric acid, 2,2'-diaminopimelic acid, 2,3-diaminopropionic acid, and cis-4-amino-L-proline. Multi-functional unnatural amino acids are available from Sigma-Aldrich.

In some embodiments, the branched core may comprise a homopolymeric multi-functional amino acid sequence, for example a poly-lysine, poly-arginine, or poly-ornithine sequence, such as a branched core comprising from two to ten, or from two to six, consecutive lysine, arginine, or ornithine residues. In other embodiments, the branched core may comprise different multi-functional amino acid residues, for example one or more lysine residues, one or more arginine residues, and/or one or more ornithine residues.

In other embodiments, the branched core may comprise a plurality of multi-functional amino acid residues, and one or more other amino acid residues.

Where the branched core comprises a plurality of multi-functional amino acid residues, adjacent multi-functional amino acid residues may be linked together by amino acid side chain links, by peptide bonds, or some adjacent multi-functional amino acid residues may be linked together by side chain links and others by peptide bonds.

In further embodiments, the branched core may comprise two or more multi-functional amino acid residues, and at least one fibrinogen-binding peptide is separately attached to each of two or more of the multi-functional amino acid residues, and two or more fibrinogen-binding peptides are separately attached to at least one of the multi-functional amino acid residues of the branched core.

According to other embodiments, two fibrinogen-binding peptides are separately attached to a terminal multi-functional amino acid residue of the branched core.

Examples of structures of peptide dendrimers of the invention include peptide dendrimers in which:
- the branched core comprises a first tri-functional amino acid residue to which two fibrinogen-binding peptides are attached, and a second tri-functional amino acid residue to which one fibrinogen-binding peptide is attached;
- the branched core comprises a first tri-functional amino acid residue to which two fibrinogen-binding peptides are attached, and a second tri-functional amino acid residue to which two fibrinogen-binding peptides are attached;
- the branched core comprises a first tri-functional amino acid residue to which two fibrinogen-binding peptides are attached, a second tri-functional amino acid residue to which one fibrinogen-binding peptide is attached, and a third tri-functional amino acid residue to which one fibrinogen-binding peptide is attached; or
- the branched core comprises a first tri-functional amino acid residue to which two fibrinogen-binding peptides are attached, a second tri-functional amino acid residue to which one fibrinogen-binding peptide is attached, a third tri-functional amino acid residue to which one fibrinogen-binding peptide is attached, and a fourth tri-functional amino acid residue to which one fibrinogen-binding peptide is attached.

A peptide dendrimer of the invention may comprise the following general formula (I):

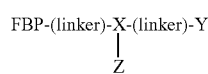
(I)

where:
FBP is a fibrinogen-binding peptide;
-(linker)- is an optional linker, preferably a non-peptide linker;
X is a tri-functional amino acid residue, preferably lysine, ornithine, or arginine;
Y is -FBP, or —NH$_2$;
Z is -(linker)-FBP when Y is -FBP, or -[—X$_n$-(linker)-FBP]$_a$-(linker)-FBP when Y is —NH$_2$;
where:
X$_n$ is a tri-functional amino acid residue, preferably lysine, L-ornithine, or arginine; and
a is 1-10, preferably 1-3.

For example, when Y is NH$_2$, Z is -[—X$_n$-(linker)-FBP]$_a$-(linker)-FBP, the structure of the dendrimer is as follows:
where a is 1:

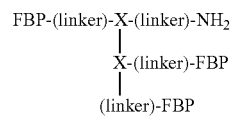

or, where a is 2:

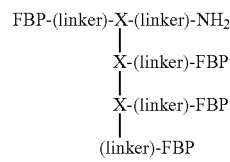

or, where a is 3:

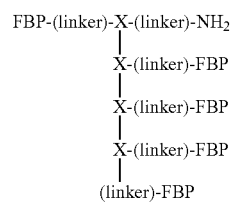

Alternatively, Z is -[—X$_n$-(linker)-FBP]$_a$-(linker)-FBP when Y is -FBP;
where:
X$_n$ is a tri-functional amino acid residue, preferably lysine, L-ornithine, or arginine; and
a is 1-10, preferably 1-3.

For example, when Y is -FBP, Z is -[—X$_n$-(linker)-FBP]$_a$-(linker)-FBP and a is 1, the structure of the dendrimer is as follows:

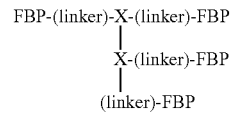

A peptide dendrimer of the invention may comprise the following general formula (II):

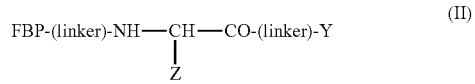
(II)

where:
 FBP is a fibrinogen-binding peptide;
 -(linker)- is an optional linker, preferably comprising —NH(CH$_2$)$_5$CO—;
 Y is -FBP, or —NH$_2$;
 Z is:

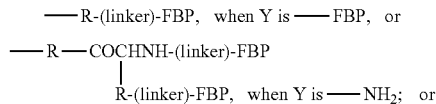

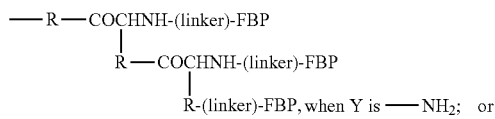

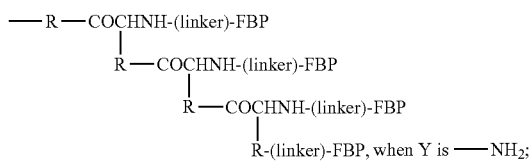

where R is —(CH$_2$)$_4$NH—, —(CH$_2$)$_3$NH—, or —(CH$_2$)$_3$NHCNHNH—.

Consequently, in one embodiment, Z may be:

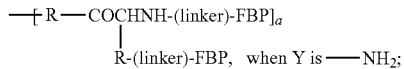

where R is —(CH$_2$)$_4$NH—, —(CH$_2$)$_3$NH—, or —(CH$_2$)$_3$NHCNHNH—;
where a is 1-3.
 Alternatively, a may be 4-10, or it may be 1-10.
 In another embodiment, Z is:

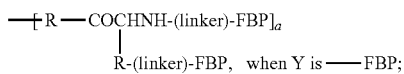

where R is —(CH$_2$)$_4$NH—, —(CH$_2$)$_3$NH—, or —(CH$_2$)$_3$NHCNHNH—;
where a is 1-10, preferably 1-3.
 For example, Z is:

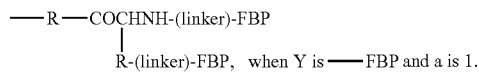

A peptide dendrimer of the invention may comprise the following general formula (III):

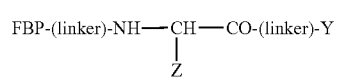

(III)

where:
 FBP is a fibrinogen-binding peptide;
 -(linker)- is an optional linker, preferably comprising —NH(CH$_2$)CO—;
 Y is -FBP, or —NH$_2$;
 Z is:

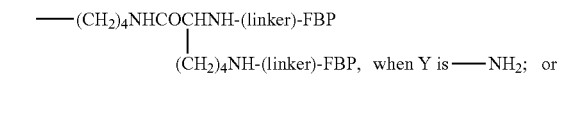

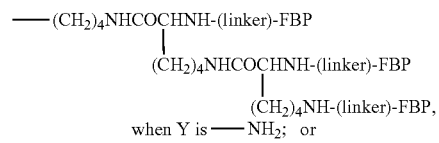

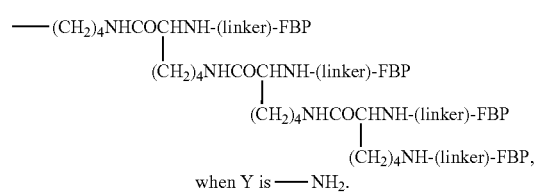

Consequently, in one embodiment, Z may be:

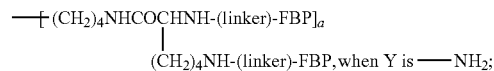

where a is 1-3.
 Alternatively a is 4-10, or it may be 1-10.
 In another embodiment, Z is:

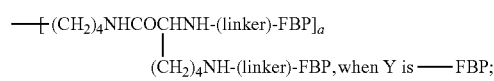

where a is 1-10, preferably 1-3.
 For example, Z is:

In one embodiment, the peptide dendrimer does not comprise the following structure:

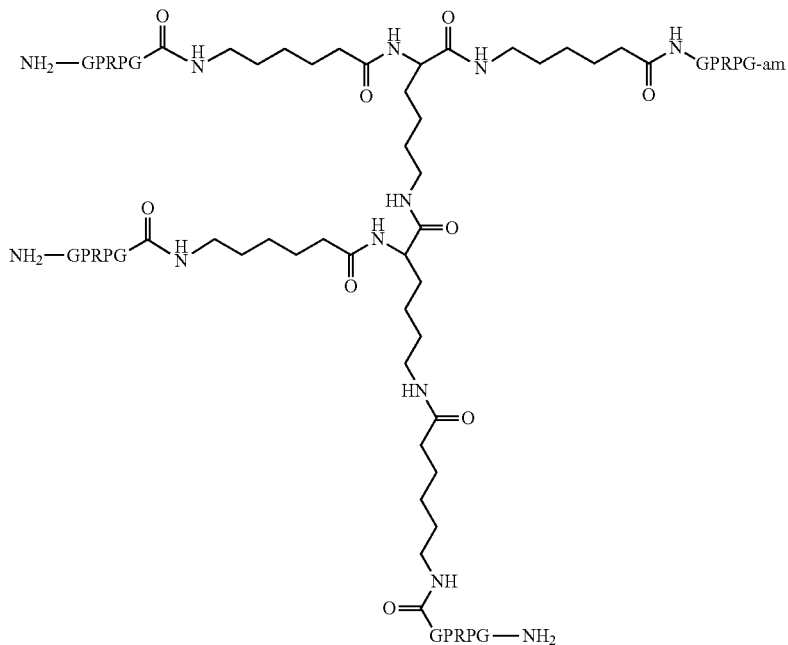

Any suitable fibrinogen-binding peptide (FBP) may be used. For example, the peptide may be capable of binding to a region of fibrinogen that is naturally bound to fibrin or by the platelet membrane glycoproteins GPIIb-IIIa. Fibrin binding to fibrinogen is discussed in Mosesson et al. 2001, *Ann. N.Y. Acad. Sci.*, 936, 11-30. Binding of GPIIb-IIIa to fibrinogen is discussed in Bennett, 2001, *Annals of NY Acad. Sci.*, 936, 340-354.

The term "peptide" as used herein also incorporates peptide analogues. Several peptide analogues are known to the skilled person. Any suitable analogue may be used provided fibrinogen is able to bind the fibrinogen binding peptide.

Examples of suitable fibrinogen binding peptides and how they may be identified are provided in WO 2005/035002, WO 2007/015107 and WO 2008/065388.

Preferably the fibrinogen-binding peptides are each 3-60, preferably 3-30, more preferably 3-10, amino acid residues in length.

Preferably each fibrinogen binding peptide binds to fibrinogen with a dissociation constant ($K_D$) of between $10^{-9}$ to $10^{-6}$ M, for example around 10, 20, 30, 40, 50, 60, 70, 80, 90, 100, 110, 120, 130, 140, 150, 200, 250, 300, 350, 400, or more nM. A $K_D$ of around 100 nM is preferred. The dissociation constant can be measured at equilibrium. For example, radio-labelled fibrinogen of known concentration can be incubated with microspheres to which the fibrinogen binding moiety has been cross-linked. Typically 5 μM peptide is cross-linked to 1 gm microspheres, or 15-40 μmoles of peptide is cross-linked to 1 gm of microspheres. The peptide-linked microspheres are diluted to 0.5 mg/ml, and incubated in isotonic buffer at pH 7.4 (for example 0.01M Hepes buffer containing 0.15M NaCl) with radio labelled fibrinogen at concentrations of between 0.05 and 0.5 mg/ml for up to 1 hr at 20° C. The fibrinogen bound to the fibrinogen binding moiety on the microspheres can be separated from the free fibrinogen by centrifugation and the amount of free and bound fibrinogen measured. The dissociation constant can then be calculated by Scatchard analysis by plotting concentration of bound fibrinogen against the ratio of the concentrations of bound: free fibrinogen, where the slope of the curve represents $K_D$.

According to some embodiments, the fibrinogen-binding peptides of peptide dendrimers of the invention bind preferentially to hole 'a' of fibrinogen over hole 'b' of fibrinogen. Examples of sequences of suitable fibrinogen-binding peptides that bind preferentially to hole 'a' over hole 'b' of fibrinogen include: GPR-; GPRP- (SEQ ID NO: 1); GPRV- (SEQ ID NO: 2); GPRPFPA- (SEQ ID NO: 3); GPRWAA- (SEQ ID NO: 4); GPRPWER- (SEQ ID NO: 5); GPRPAA- (SEQ ID NO: 6); GPRPPEC- (SEQ ID NO: 7); GPRPPER- (SEQ ID NO: 8); GPSPAA- (SEQ ID NO: 9).

According to other embodiments, the fibrinogen-binding peptides of peptide dendrimers of the invention bind preferentially to hole 'b' of fibrinogen over hole 'a' of fibrinogen. Examples of sequences of fibrinogen-binding peptides that bind preferentially to hole 'b' over hole 'a' of fibrinogen include: GHR-, GHRP- (SEQ ID NO: 10), GHRPY- (SEQ ID NO: 11), GHRPL- (SEQ ID NO: 12), GHRPYamide- (SEQ ID NO: 13).

Each fibrinogen-binding peptide of a peptide dendrimer of the invention may, independently, be attached at its carboxy-terminal end (optionally via a linker), or at its amino-terminal end (optionally via a linker) to the branched core of the dendrimer. If the fibrinogen-binding peptide is attached at its amino-terminal end, the carboxy-terminal end of the peptide may comprise an amide group. The presence of an amide group, rather than a carboxyl group (or a negatively charged carboxylate ion), at the exposed carboxy-terminal end of the peptide may help to optimise binding of the fibrinogen-binding peptide to fibrinogen.

In some embodiments, each fibrinogen-binding peptide is attached (optionally via a linker) at its carboxy-terminal end to the branched core of the dendrimer. In other embodiments, at least one fibrinogen-binding peptide is attached (optionally via a linker) at its amino-terminal end to the branched core of the dendrimer. For example, at least one fibrinogen-binding peptide that binds preferentially to hole 'a' over hole 'b' of fibrinogen, such as a peptide comprising sequence APFPRPG (SEQ ID NO: 14), may be attached (optionally via a linker) at its amino-terminal end to the branched core of the dendrimer.

Advantageously, a peptide dendrimer of the invention comprises fibrinogen-binding peptides of different sequence (referred to herein as a 'chimeric' peptide dendrimer). For example, in some embodiments a peptide dendrimer of the invention comprises fibrinogen-binding peptides that have different selectivity of binding to hole 'a' over hole 'b' of fibrinogen.

According to a second aspect of the invention there is provided an agent that comprises a plurality of carriers, wherein each carrier has a plurality of fibrinogen-binding peptides attached to the carrier, and wherein the fibrinogen-binding peptides attached to the carriers comprise fibrinogen-binding peptides of different sequence.

In some embodiments of the second aspect of the invention, the plurality of carriers comprise a first plurality of carriers, and a second plurality of carriers, wherein the fibrinogen-binding peptides attached to the first plurality of carriers are of different sequence to the fibrinogen-binding peptides attached to the second plurality of carriers.

In other embodiments of the second aspect of the invention, each carrier has fibrinogen-binding peptides of different sequence attached thereto.

The carrier may be a soluble or insoluble carrier, but is preferably not a platelet. The carrier may be suitable for topical administration to a tissue site of a subject, for example a bleeding wound site, or a mucosal site. Soluble carriers may be suitable for intravenous rather than topical administration. The carrier may comprise a soluble or insoluble protein, a therapeutic drug, a polymer (for example a biocompatible polymer, such as polyethylene glycol), or a combination of any of these. Examples of protein carriers are an enzyme or a protein which is not an enzyme, such as human serum albumin.

An insoluble carrier may be a microparticle (including a solid, hollow, or porous microparticle, preferably a substantially spherical microparticle). The microparticle may be formed of any suitable substance, for example cross-linked protein. A suitable protein is albumin (serum-derived or recombinant, human or non-human in sequence) or gelatin. Microparticles suitable for use as insoluble carriers in the present invention may be formed by spray drying human serum albumin (HSA) using well known spray-drying technology, for example as in WO 92/18164. Alternatives to use of microparticles as carriers include liposomes, synthetic polymer particles (such as polylactic acid, polyglycolic acid and poly(lactic/glycolic) acid), or cell membrane fragments.

At least a majority of the carriers may have a maximum dimension that is less than 6 μm. This may be preferred if the agents of the invention are for intravenous administration.

Alternatively, at least a majority of the carriers may have a maximum dimension that is greater than 6 m. This may be preferred if the agents of the invention are for topical administration.

In theory there is no upper limit to the number of fibrinogen-binding peptides per carrier molecule. The optimum number is likely to depend on many factors, such as the nature of the carrier, and the number of reactive groups on each carrier for attaching the fibrinogen-binding peptides. However, it is preferred that on average there are up to 100 fibrinogen-binding peptides per carrier molecule. Preferably, on average there are at least three, preferably at least four or five fibrinogen-binding peptides per carrier molecule. A preferred range is 10-20 fibrinogen-binding peptides per carrier molecule.

The carrier may comprise groups which permit attachment of the fibrinogen-binding peptides to the carrier. For example, the carrier may comprise thiol moieties or amine moieties on its surface. If the carrier is proteinaceous, the thiol or amine moieties may be provided by side chains of amino acids, for example cysteine or lysine. Non-peptide groups may be added to the carrier. This is particularly advantageous if the carrier is formed from protein, such as HSA. For example, thiol groups may be added to the carrier using reagents such as 2-iminothiolane (2-IT) which is able to react with primary amine groups on the carrier.

The fibrinogen-binding peptides of different sequence may comprise a first fibrinogen-binding peptide that binds preferentially to hole 'a' over hole 'b' of fibrinogen, and a second fibrinogen-binding peptide that binds with higher selectivity to hole 'a' over hole 'b' of fibrinogen than the first fibrinogen-binding peptide. Such peptide dendrimers have been found to polymerise fibrinogen rapidly over a relatively wide range of peptide dendrimer concentration.

For example, the first fibrinogen-binding peptide may comprise an amino acid sequence GPRP- (SEQ ID NO: 1) at its amino-terminal end, and/or the second fibrinogen-binding peptide may comprise an amino acid sequence -APFPRPG (SEQ ID NO: 14) at its carboxy-terminal end, where the amino acid residues of the sequences are denoted in amino- to carboxy-order, and "-" denotes the end of the sequence that is attached to the branched core of the peptide dendrimer, or to the carrier. A fibrinogen-binding peptide with the sequence -APFPRPG (SEQ ID NO: 14) at its carboxy-terminal end binds with higher selectivity to hole 'a' over hole 'b' of fibrinogen than a fibrinogen-binding peptide with the sequence GPRP- (SEQ ID NO: 1) at its amino-terminal end.

In other embodiments, the fibrinogen-binding peptides of different sequence may comprise a first fibrinogen-binding peptide that binds preferentially to hole 'a' over hole 'b' of fibrinogen, and a second fibrinogen-binding peptide that binds preferentially to hole 'b' over hole 'a' of fibrinogen. Such peptide dendrimers have been found to polymerise with fibrinogen to form relatively dense hydrogels compared to equivalent peptide dendrimers containing only fibrinogen-binding peptides that bind preferentially to hole 'a' over hole 'b' of fibrinogen. It is believed that the increased density of the hydrogels formed is due to binding of fibrinogen-binding peptides of the dendrimers to hole 'a' and hole 'b' of fibrinogen, thereby strengthening the network of polymerised fibrinogen.

For example, the first fibrinogen-binding peptide may comprise an amino acid sequence GPRP- (SEQ ID NO: 1) at its amino-terminal end and/or the second fibrinogen-binding peptide may comprise an amino acid sequence GHRP- (SEQ ID NO: 10), or an amino acid sequence GHRPY- (SEQ ID NO: 11), at its amino terminal end. Fibrinogen-binding peptides with the sequence GPRP- (SEQ ID NO: 1) at the amino-terminal end bind with some selectivity to hole 'a' of fibrinogen. Fibrinogen-binding peptides with the sequence GHRP- (SEQ ID NO: 10), or GHRPY- (SEQ ID NO: 11), at the amino-terminal end bind preferentially to hole 'b' of fibrinogen.

One or more, or each, fibrinogen-binding peptide may be covalently attached to the branched core of a peptide dendrimer of the invention by a non-peptide linker. The linker may be any suitable linker that does not interfere with binding of fibrinogen to fibrinogen-binding peptides of the peptide dendrimer. The linker may comprise a flexible, straight-chain linker, suitably a straight-chain alkyl group. Such linkers allow the fibrinogen-binding peptides of the peptide dendrimer to extend away from each other. For example, the linker may comprise a —NH(CH$_2$)$_n$CO— group, where n is any number, suitably 1-10, for example 5. A linker comprising a —NH(CH$_2$)$_5$CO— group may be formed by use of ε-amino acid 6-aminohexanoic acid (εAhx).

In theory, there is no limit to the total number of fibrinogen-binding peptides that may be present in a peptide dendrimer of the invention. However, in practice, for any particular structure, the number of fibrinogen-binding peptides can be varied and tested to determine the optimum number for the desired fibrinogen polymerisation properties, for example, for the speed fibrinogen polymerisation or for the density of the hydrogel produced by polymerisation with fibrinogen. Peptide dendrimers may comprise a total of up to twenty fibrinogen-binding peptides per dendrimer, for example up to ten fibrinogen-binding peptides per dendrimer, or up to five fibrinogen-binding peptides per dendrimer.

The Applicant has found that, surprisingly, mixtures of a peptide dendrimer of the invention with a peptide conjugate, comprising two or more fibrinogen-binding peptides, are able to polymerise fibrinogen more rapidly than either the peptide dendrimer, or the peptide conjugate, alone.

According to the invention there is provided a composition comprising a peptide dendrimer of the invention, and a peptide conjugate comprising two or more fibrinogen-binding peptides.

The peptide conjugate may comprise fibrinogen-binding peptides of the same sequence, or of different sequence. For example, the peptide conjugate may comprise only fibrinogen-binding peptides that bind preferentially to hole 'a' over hole 'b' of fibrinogen, or only fibrinogen-binding peptides that bind preferentially to hole 'b' over hole 'a' of fibrinogen, or one or more fibrinogen-binding peptides that bind preferentially to hole 'a' over hole 'b' of fibrinogen and one or more fibrinogen-binding peptides that bind preferentially to hole 'b' over hole 'a' of fibrinogen.

The peptide conjugate may comprise a carrier to which the fibrinogen-binding peptides are attached. A suitable carrier may comprise one or more amino acid residues, for example a single amino acid residue, such as a lysine amino acid residue. An advantage of conjugates comprising carriers that comprise one or more amino acid residues is that they can readily be made using solid-phase peptide synthesis methods.

Each fibrinogen-binding peptide of the peptide conjugate may, independently, be attached at its carboxy-terminal end (optionally via a linker), or at its amino-terminal end (optionally via a linker), to the carrier. If the fibrinogen-binding peptide is attached at its amino-terminal end, the carboxy-terminal end of the peptide may comprise an amide group.

In some embodiments, the peptide conjugate may be a peptide dendrimer of the invention.

The fibrinogen-binding peptides of the peptide dendrimer of a composition of the invention may bind preferentially to hole 'a' of fibrinogen over hole 'b' of fibrinogen, and the fibrinogen-binding peptides of the peptide conjugate may bind preferentially to hole 'b' of fibrinogen over hole 'a' of fibrinogen.

Such compositions have been found to have synergistic effects in that they are able to polymerise fibrinogen more rapidly than either the peptide dendrimer or the peptide conjugate alone. The mechanism of this synergistic effect is not fully understood, but without being bound by theory, it is believed that it may occur because the composition provides more 'A' and 'B' fibrinogen polymerisation sites.

Alternatively, the fibrinogen-binding peptides of the peptide dendrimer of a composition of the invention may bind preferentially to hole 'b' of fibrinogen over hole 'a' of fibrinogen, and the fibrinogen-binding peptides of the peptide conjugate bind preferentially to hole 'a' of fibrinogen over hole 'b' of fibrinogen.

According to the invention there is also provided a pharmaceutical composition, which comprises a peptide dendrimer of the invention, an agent of the invention, or a composition of the invention, and a pharmaceutically acceptable carrier, excipient, or diluent.

Suitable pharmaceutically acceptable carriers, excipients, and diluents are well-known to the skilled person. Pharmaceutically acceptable carriers, excipients, and diluents include those suitable for topical administration with a peptide dendrimer, an agent, or a composition, of the invention to a wound site. Examples of suitable pharmaceutically acceptable carriers include carriers, preferably in flowable form, such as gelatin, fibrin, chitosan, fibronectin, collagen, starch, hyaluronic acid. Suitable pharmaceutically acceptable diluents or excipients include buffers, such as Tris-HCl, acetate, or phosphate buffers, additives such as detergents or solubilizing agents (for example, Tween 80, Polysorbate 80), anti-oxidants (for example, ascorbic acid, sodium metabisulfite), preservatives (for example, meta-cresol, parabens (methyl, propyl, or butyl), chlorobutanol, phenylmercuric salts (for example, acetate, borate, nitrate), sorbic acid, benzyl alcohol), and bulking substances (for example, lactose, mannitol), tonicity agents (for example, sugars, sodium chloride), polymeric compounds, such as polylactic acid, polyglycolic acid.

A particular advantage of peptide dendrimers, agents, and compositions, of the invention is that they can readily be sterilised, for example by exposure to irradiation, suitably gamma irradiation, without significant loss of the ability of the peptide dendrimer, or composition, to polymerise with fibrinogen.

According to the invention, there is provided a method of sterilising a peptide dendrimer of the invention, an agent of the invention, or a composition of the invention, which comprises exposing the peptide dendrimer, agent, or composition to gamma irradiation, preferably up to 30 kGy. The peptide dendrimer, agent, or composition may be in dry, wet, or solvent form.

According to the invention there is also provided a peptide dendrimer of the invention, an agent of the invention, or a composition of the invention, which is sterile.

Peptide dendrimers, agents, or compositions, of the invention may advantageously be provided as a sterile, ready-to-use formulation, in particular, as a sterile, ready-to-use haemostatic or wound treatment formulation.

In some embodiments, a peptide dendrimer of the invention may be formulated into a hydrated flowable gelatin paste and packaged into a syringe that can be irradiated to provide a sterile, ready-to-use, flowable product.

According to the invention, there is also provided a method of polymerising fibrinogen, which comprises contacting fibrinogen with a peptide dendrimer of the invention, with an agent of the invention, or with a composition of the invention.

The relative concentration of the dendrimer and the fibrinogen used for polymerisation will depend on the nature of the dendrimer, for example how many fibrinogen-binding peptides are present, and the sequence of the fibrinogen-binding peptides. The Applicant has observed rapid polymerisation times using peptide dendrimers of the invention at concentrations ranging from 0.005 mg/ml to 2 mg/ml with physiological levels of fibrinogen (3 mg/ml).

For some peptide dendrimers of the invention, as the concentration of the dendrimer is increased, the speed of fibrinogen polymerisation (i.e. the "clotting time") is reduced. Without being bound by theory, this is believed to be due to saturation of the 'a' and/or 'b' holes of the fibrinogen molecules by the fibrinogen-binding peptides of the dendrimer. At these higher dendrimer concentrations, there is an excess of fibrinogen-binding peptides competing for free fibrinogen binding holes (i.e. for empty 'a' and/or 'b' holes), and this competition is believed to reduce the rate at which polymerisation takes place.

There is also provided according to the invention a kit for formation of a hydrogel, which comprises a peptide dendrimer of the invention, an agent of the invention, or a composition of the invention, and, separately, fibrinogen.

There is further provided according to the invention a hydrogel comprising a copolymer of a peptide dendrimer of the invention, of an agent of the invention, or of a composition of the invention, and fibrinogen.

Peptide dendrimers, agents, and compositions of the invention may be used as haemostatic agents, for example to treat bleeding, or to treat a wound.

According to the invention there is provided a method of treating bleeding, or of treating a wound, which comprises administering a peptide dendrimer of the invention, an agent of the invention, or a composition of the invention, to a site of bleeding or to a wound.

The peptide dendrimer, agent, or composition, may polymerise endogenous (i.e. host) fibrinogen present at the site of bleeding or the wound. In some embodiments, exogenous fibrinogen may be administered as well as the peptide dendrimer, the agent, or the composition, of the invention to the site of bleeding or to the wound.

The term "fibrinogen" is used herein to include natural fibrinogen, recombinant fibrinogen, or a derivative of fibrinogen that can be converted by thrombin to form fibrin (for example, natural or recombinant fibrin monomer, or a derivative of fibrin monomer that may or may not be capable of spontaneous assembly). The fibrinogen should be able to bind at least two fibrinogen binding peptides. The fibrinogen may be obtained from any source, and from any species (including bovine fibrinogen), but is preferably human fibrinogen. Human fibrinogen may be obtained from autologous or donor blood. Autologous fibrinogen, or recombinant fibrinogen, is preferred because this reduces the risk of infection when administered to a subject.

A suitable amount of the peptide dendrimer for administration to a human subject will depend, for example, on the type of dendrimer, for example how many fibrinogen-binding peptides are present per dendrimer molecule, and on the type and size of wound or bleeding site. However, a typical amount of the dendrimer is 0.1 ml to 50 ml, for example 0.1 ml to 5 ml, or 1 to 50 ml, of a preparation (for example, an aqueous preparation) containing the dendrimer at a concentration of 0.005 to 25 mg/ml.

A suitable amount of exogenous fibrinogen for administration to a human subject is from 0.1 mg to 200 mg, for example 3 mg to 200 mg.

Peptide dendrimers, agents, or compositions of the invention may be provided as a fluid for administration directly to a wound, or applied to a sponge or fabric (for example, impregnated or coated), optionally with fibrinogen, prior to application. Alternatively, peptide dendrimers, agents, or compositions of the invention may be mixed with a flowable paste for administration with a syringe.

According to the invention there is also provided a peptide dendrimer of the invention, an agent of the invention, or a composition of the invention, for use as a medicament.

There is further provided according to the invention a peptide dendrimer of the invention, an agent of the invention, or a composition of the invention, for use in the treatment of bleeding or for use in treating a wound.

There is also provided according to the invention use of a peptide dendrimer of the invention, an agent of the invention, or a composition of the invention, in the manufacture of a medicament for use in the treatment of bleeding or for use in treating a wound.

Peptide dendrimers, agents, and compositions, of the invention have several important advantages. In particular, in certain embodiments, the peptide dendrimers, agents, and compositions, can readily be manufactured using conventional solid-phase peptide synthesis procedures. At optimum concentrations, peptide dendrimers, agents, and compositions, of the invention can polymerise fibrinogen, in the absence of thrombin, in less than a second. Peptide dendrimers and agents of the invention can also polymerise fibrinogen in human plasma in less than a second.

The structure of a peptide dendrimer or agent of the invention can be selected so as to optimise its properties for the intended use of the dendrimer. For example, a peptide dendrimer comprising five fibrinogen-binding peptides of the same sequence that bind preferentially to the 'a' hole of fibrinogen is able to polymerise fibrinogen almost instantaneously. In contrast, a 'chimeric' peptide dendrimer with one or more fibrinogen-binding peptides that bind preferentially to the 'a' hole of fibrinogen, and one or more different fibrinogen-binding peptides that bind preferentially to the 'b' hole of fibrinogen, may polymerise fibrinogen more slowly, but forms hydrogels of greater density and size.

Peptide dendrimers, agents, and compositions, of the invention can be sterilised without loss of fibrinogen polymerisation activity. This is an important advantage because it allows the peptide dendrimers, agents, and compositions to be provided in sterile, ready-to-use, formulations, for example as ready-to-use haemostatic or wound treatment formulations.

Embodiments of the invention are now described by way of example only, with reference to the accompanying drawings in which.

EXAMPLE 1

Figure 1:
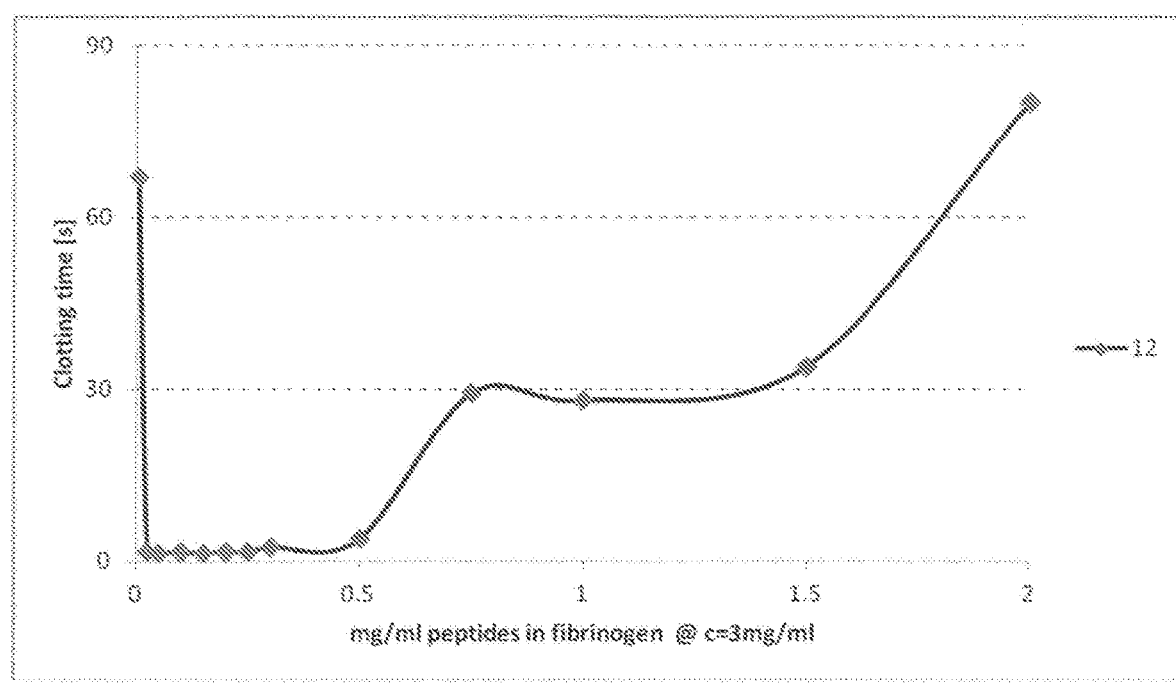
FIG. 1 shows the ability of a peptide dendrimer of a preferred embodiment to polymerise fibrinogen at varying concentrations.

Synthesis of Peptide Dendrimers and Peptide Conjugates

Peptides were synthesised on Rink amide MBHA low loaded resin (Novabiochem, 0.36 mmol/g), by standard Fmoc peptide synthesis, using Fmoc protected amino acids (Novabiochem).

In general, single-coupling cycles were used throughout the synthesis and HBTU activation chemistry was employed (HBTU and PyBOP (from AGTC Bioproducts) were used as the coupling agents). However, at some positions coupling was less efficient than expected and double couplings were required.

The peptides were assembled using an automated peptide synthesiser and HBTU up to the branch points and by manual peptide synthesis using PyBOP for the peptide branches.

For automated synthesis a threefold excess of amino acid and HBTU was used for each coupling and a ninefold excess of diisopropylethylamine (DIPEA, Sigma) in dimethylformamide (DMF, Sigma).

For manual synthesis a threefold excess of amino acid and PyBOP was used for each coupling and a ninefold excess of DIPEA in N-methylpyrollidinone (NMP, Sigma).

Deprotection (Fmoc group removal) of the growing peptide chain using 20% piperidine (Sigma) in DMF likewise may not always be efficient and require double deprotection.

Branches were made using Fmoc-Lys(Fmoc)-OH, Fmoc-Lys(Boc)-OH, or Fmoc-Lys(Mtt)-OH.

Final deprotection and cleavage of the peptide from the solid support was performed by treatment of the resin with 95% TFA (Sigma) containing triisopropylsilane (TIS, Sigma), water and anisole (Sigma) (1:1:1, 5%) for 2-3 hours.

The cleaved peptide was precipitated in cold diethyl ether (Sigma) pelleted by centrifugation and lyophilized. The pellet was re-dissolved in water (10-15 mL), filtered and purified via reverse phase HPLC using a C-18 column (Phenomenex at flow rate 20 ml/min) and an acetonitrile/water gradient containing 0.1% TFA. The purified product was lyophilized and analyzed by ESI-LC/MS and analytical HPLC and were demonstrated to be pure (>95%). Mass results all agreed with calculated values.

Peptide Dendrimers and Peptide Conjugates

The structures of peptide dendrimers and peptide conjugates synthesised using the methods described above are shown below.

The "$NH_2$—" group at the end of a peptide sequence denotes an amino group at the amino-terminal end of the sequence. The "-am" group at the end of a peptide sequence denotes an amide group at the carboxy-terminal end of the sequence.

Peptide Conjugate No. 1

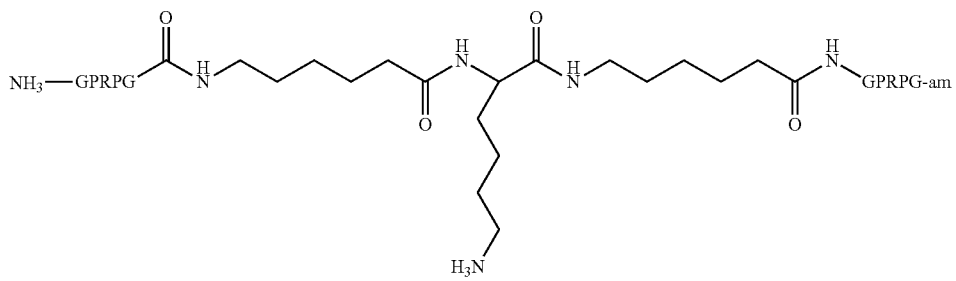

Peptide Conjugate No. 2

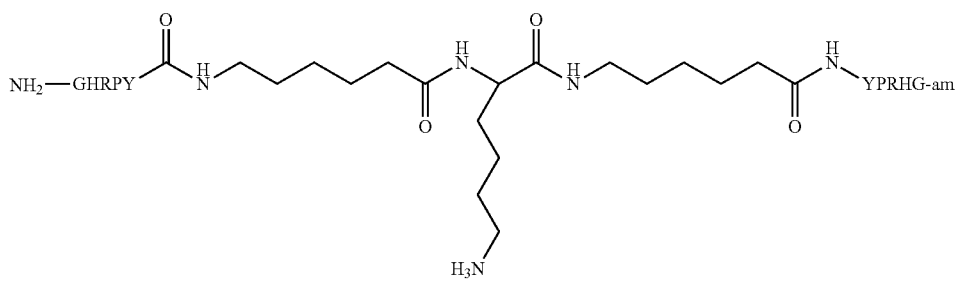

Peptide Conjugate No. 3
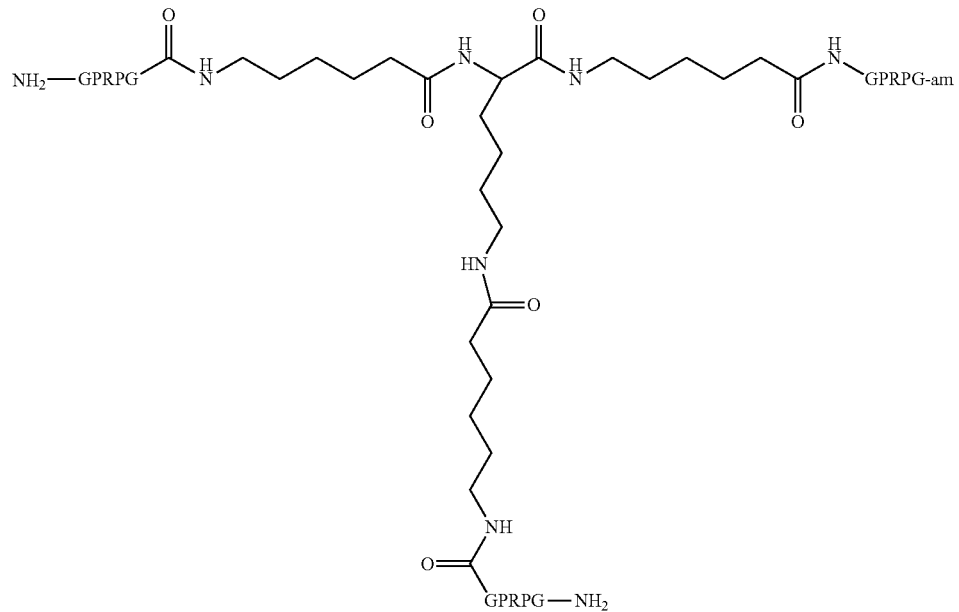
Peptide Conjugate No. 4
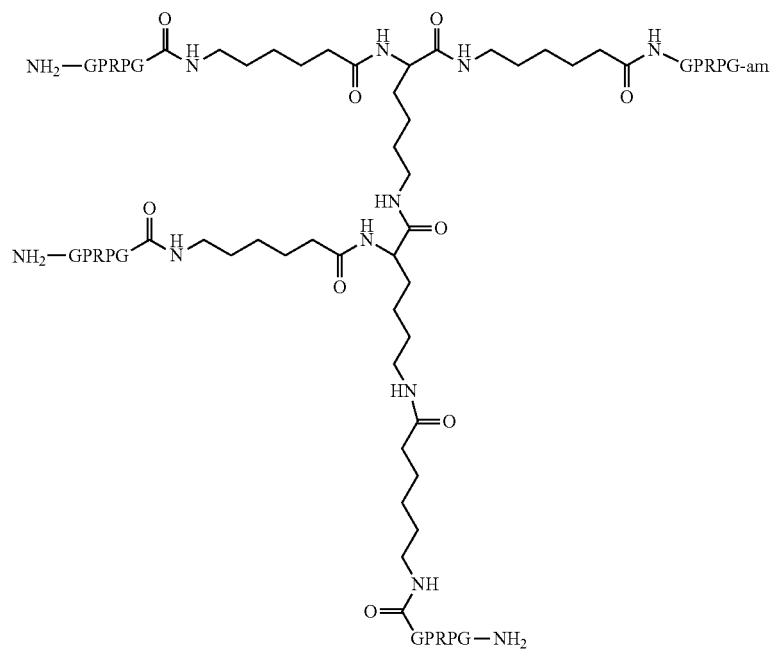

-continued
Peptide Conjugate No. 5
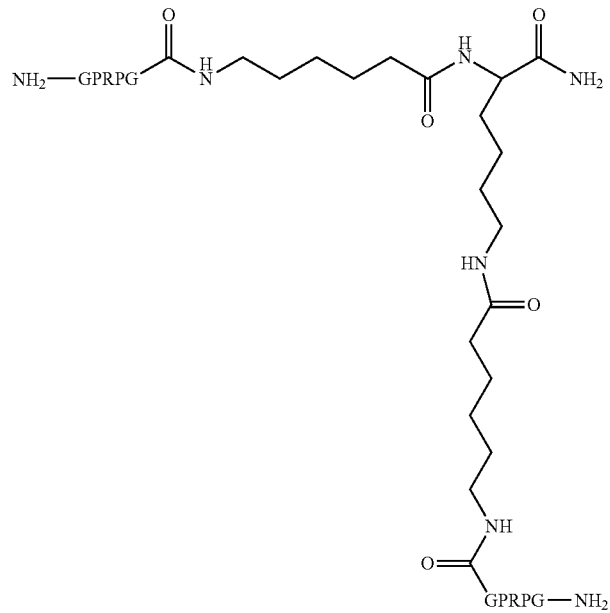
Peptide Dendrimer No. 8
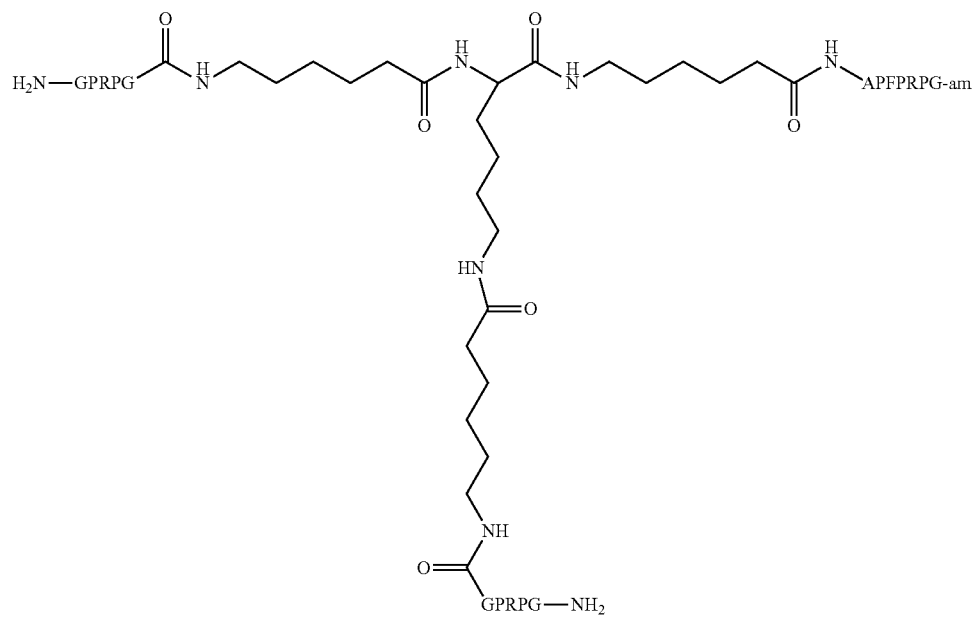

Peptide Dendrimer No. 9
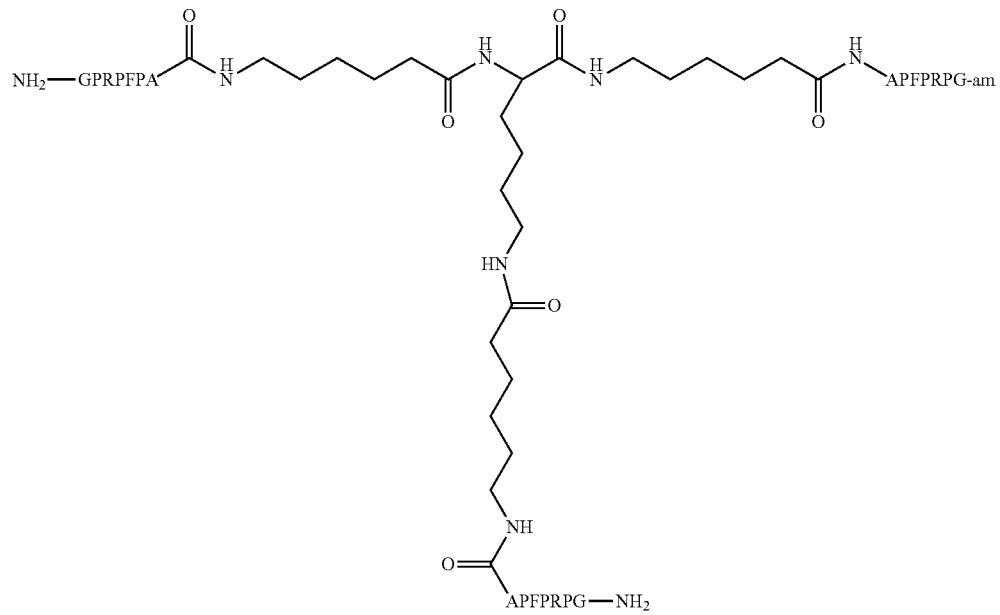
Peptide Dendrimer No. 10
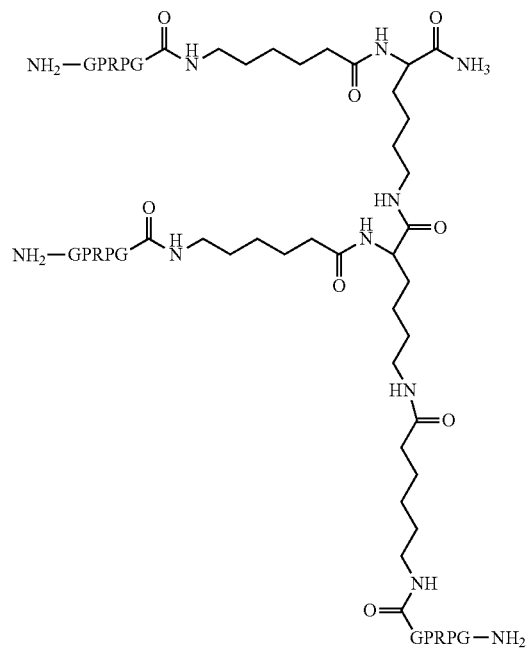

Peptide Dendrimer No. 11
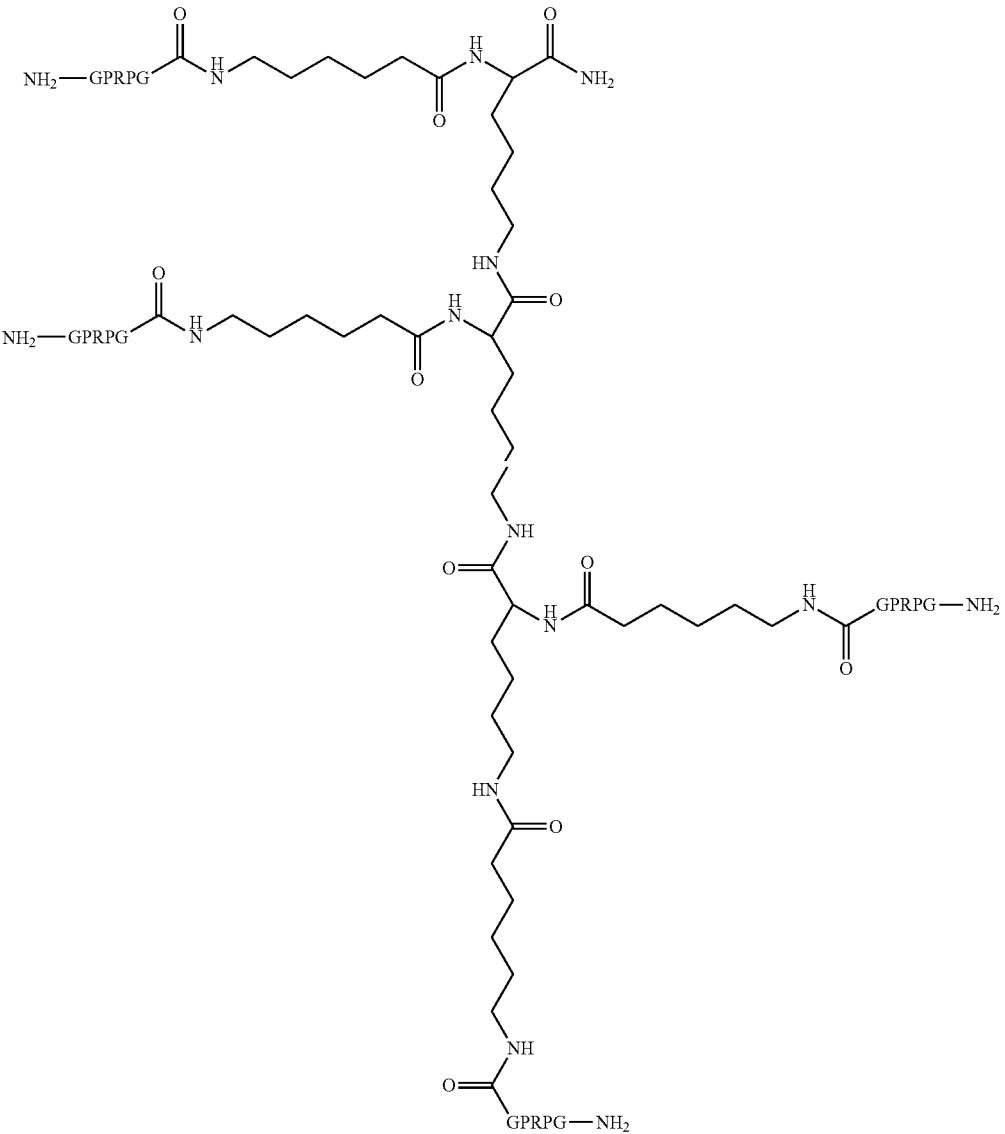
Peptide Dendrimer No. 12
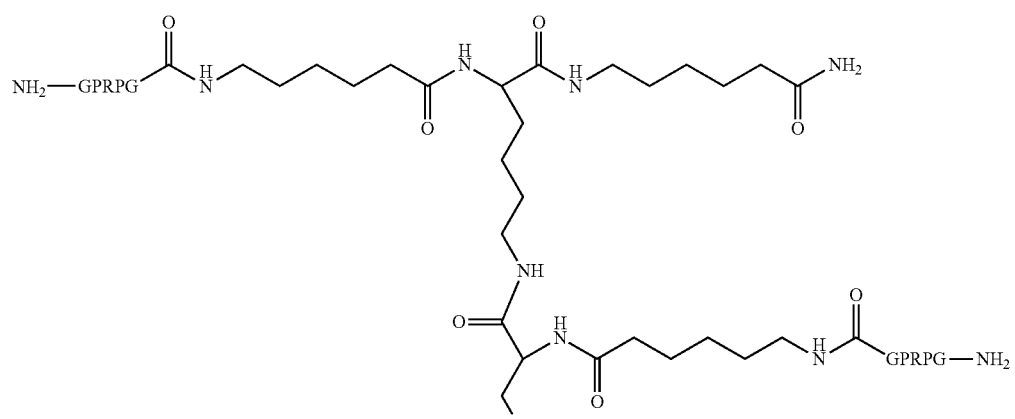

-continued
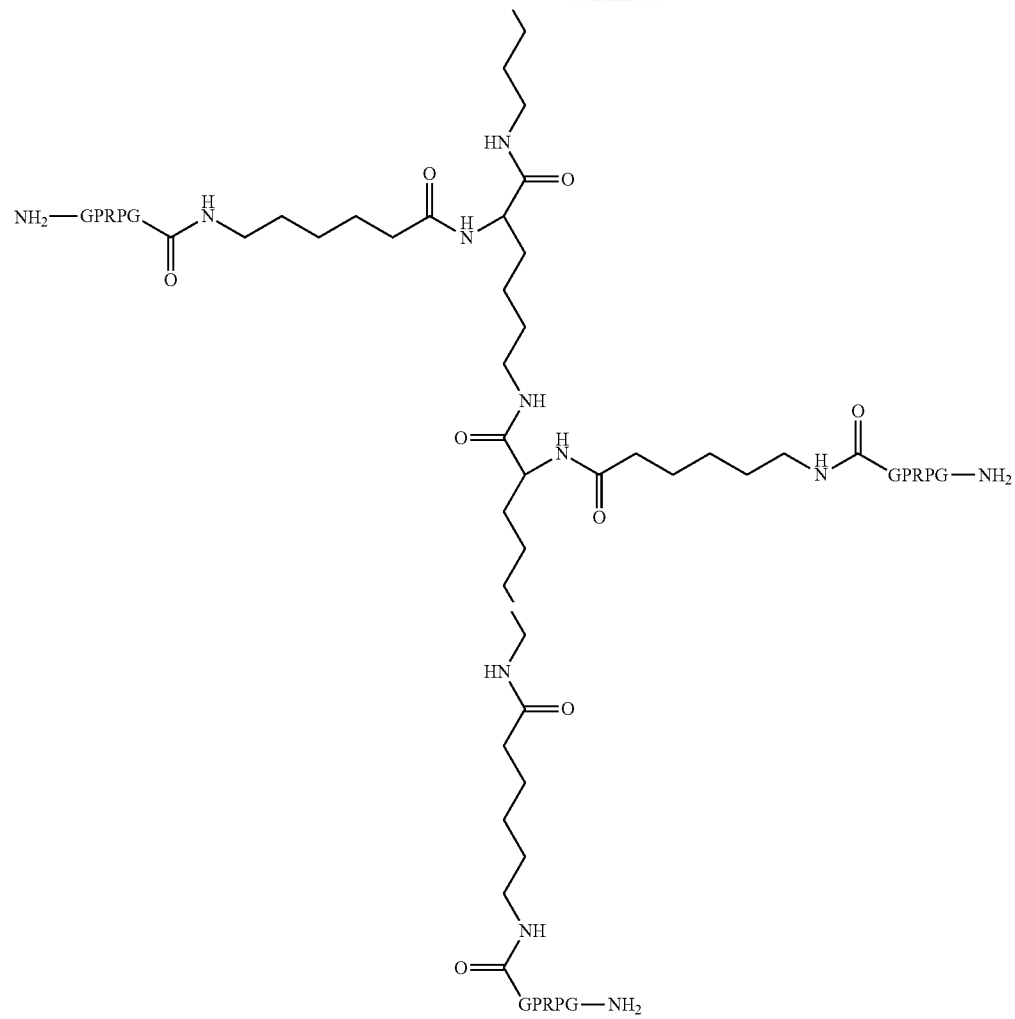
Peptide Dendrimer No. 13
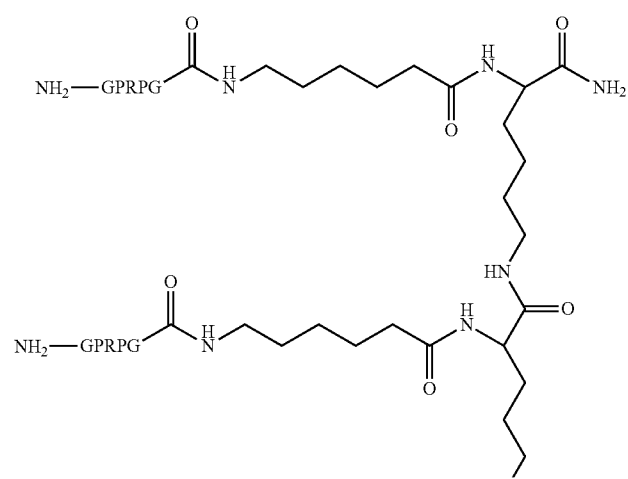

-continued

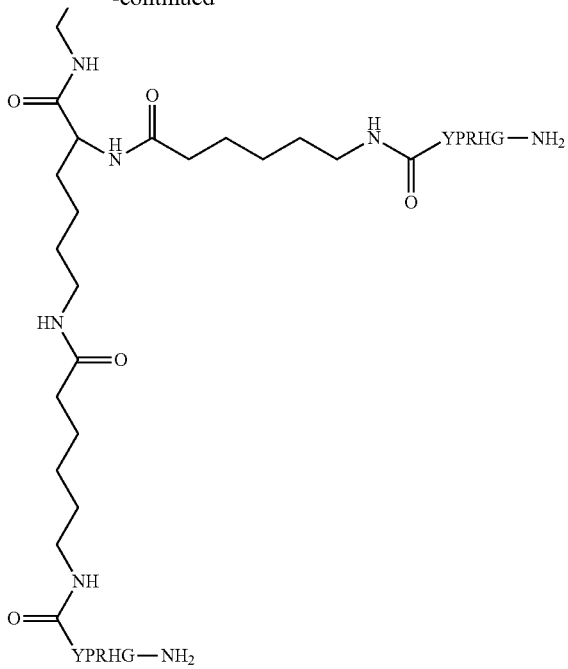

EXAMPLE 2

Copolymerisation of a Peptide Dendrimer with Fibrinogen

Dendrimer No. 12 comprises a branched core with five consecutive lysine residues. The lysine residues are covalently linked through a side chain of an adjacent lysine residue.

The ability of Peptide Dendrimer No. 12 to polymerise fibrinogen was assessed. 30 µl of dendrimer in solution, at concentration ranging from 0.005-2 mg/ml, was added to 100 µl purified human fibrinogen at 3 mg/ml (the level of fibrinogen found in the blood). Polymerisation of fibrinogen was analysed using a Sigma Amelung KC4 Delta coagulation analyser. FIG. 1 shows a plot of the polymerisation (clotting) times (in seconds) with increasing concentration of dendrimer.

The results show that the dendrimer was able to copolymerise with fibrinogen almost instantaneously, even at very low concentrations of dendrimer. The increase in clotting time with dendrimer concentrations above 0.5 mg/ml is thought to be explained by an excess of fibrinogen-binding peptides compared to the number of free binding pockets in fibrinogen. At higher concentrations, the fibrinogen-binding peptides of the dendrimer may saturate the fibrinogen binding pockets, resulting in a significant number of excess dendrimer molecules that are not able to copolymerise with fibrinogen.

EXAMPLE 3

Effect of Varying the Number of Fibrinogen-Binding Peptides Per Dendrimer on the Speed of Copolymerisation with Fibrinogen This example investigates the effect of varying the number of fibrinogen-binding peptides per peptide dendrimer on the speed of copolymerisation with fibrinogen.

Figure 2:
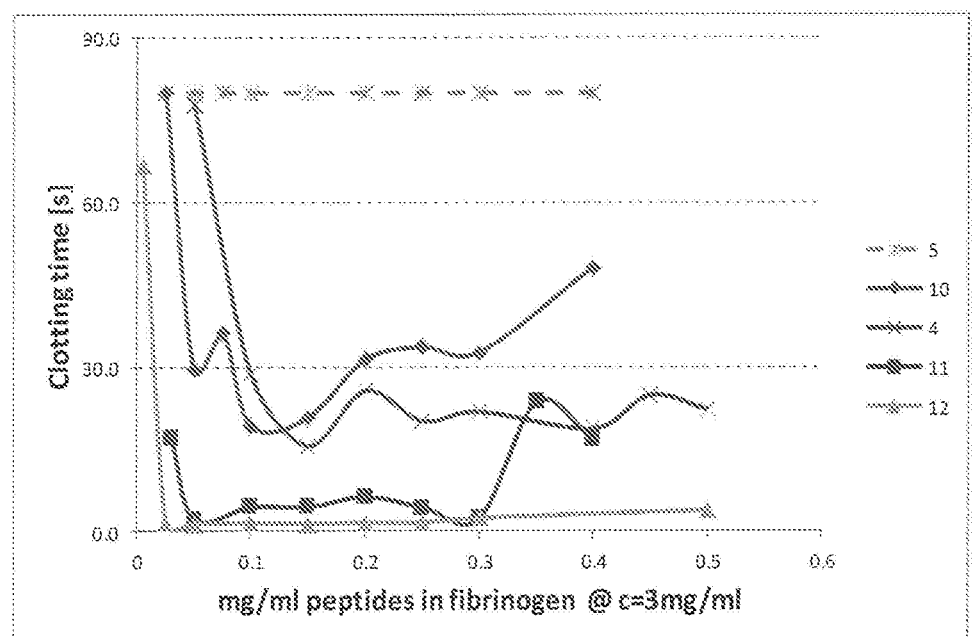
FIG. 2 shows the ability of several different peptide dendrimers to polymerise fibrinogen at varying concentrations. The numbering refers to the identity of the peptide dendrimer.

The ability of Peptide Dendrimer Nos. 4, 5, 10, 11, and 12 to copolymerise with fibrinogen was assessed using the same method described in Example 2. The concentration of each dendrimer was varied from 0.005-0.5 mg/ml. FIG. 2 shows a plot of the clotting times (in seconds) with increasing concentration of each different dendrimer.

The results show that dendrimer No. 5 (with only two fibrinogen-binding peptides/dendrimer) was not able to copolymerise with fibrinogen. As the number of fibrinogen-binding peptides was increased from three to five, at concentrations of dendrimer from ~0.125 to ~0.275 mg/ml, the speed of copolymerisation increased. At concentrations below ~0.125 mg/ml dendrimer, dendrimer No. 10 (with three fibrinogen-binding peptides/dendrimer) produced faster clotting times than dendrimer no. 4 (with four fibrinogen-binding peptides/dendrimer). In the range ~0.02-0.5 mg/ml, dendrimer no. 12 (with five fibrinogen-binding peptides/dendrimer) produced almost instantaneous clotting. In the range ~0.05-0.3 mg/ml, dendrimer no. 11 (with four fibrinogen-binding peptides/dendrimer) also produced almost instantaneous clotting.

It is concluded that the speed at which fibrinogen is polymerised by a dendrimer of the invention generally increases as the number of fibrinogen-binding peptides per dendrimer is increased.

EXAMPLE 4

Effect of Fibrinogen-Binding Peptide Orientation, and of Different Fibrinogen-Binding Peptide Sequences on Speed of Copolymerisation with Fibrinogen To assess whether the orientation of a fibrinogen-binding peptide could affect the ability of a peptide dendrimer to copolymerise with fibrinogen, peptide dendrimers comprising three fibrinogen-binding peptides attached to a single tri-functional amino acid residue (lysine) were synthesised (referred to as 'three-branch' dendrimers), but with one of the fibrinogen-binding peptides orientated with its amino-terminal end attached to the branched core, and amidated at its carboxy-terminal end. The ability of peptide dendrimers comprising different fibrinogen-binding peptide sequences to copolymerise with fibrinogen was also tested.

The fibrinogen-binding peptides of Peptide Dendrimer Nos. 3 and 10 are each of sequence GPRPG (SEQ ID NO: 15). Each fibrinogen-binding peptide of Peptide Dendrimer No. 10 is orientated with its carboxy-terminal end attached to the branched core. One of the fibrinogen-binding peptides of Peptide Dendrimer No. 3 is orientated with its amino-terminal end attached to the branched core. The carboxy-terminal end of that peptide comprises an amide group.

Two of the fibrinogen-binding peptides of Peptide Dendrimer No. 8 are of sequence GPRPG (SEQ ID NO: 15), and the third fibrinogen-binding peptide is of sequence APFPRPG (SEQ ID NO: 14) orientated with its amino-terminal end attached to the branched core. The carboxy-terminal end of that peptide comprises an amide group.

Two of the fibrinogen-binding peptides of Peptide Dendrimer No. 9 are of sequence GPRPFPA (SEQ ID NO: 3), and the third fibrinogen-binding peptide is of sequence APFPRPG (SEQ ID NO: 14) orientated with its amino-terminal end attached to the branched core. The carboxy-terminal end of that peptide comprises an amide group.

The sequence GPRPG (SEQ ID NO: 15) binds to hole 'a' and hole 'b' of fibrinogen, but with some preference for hole 'a'. The sequence GPRPFPA (SEQ ID NO: 3) binds with high preference for hole 'a' in fibrinogen. The sequence Pro-Phe-Pro stabilizes the backbone of the peptide chain and enhances the affinity of the knob-hole interaction (Stabenfeld et al., BLOOD, 2010, 116: 1352-1359).

Figure 3:
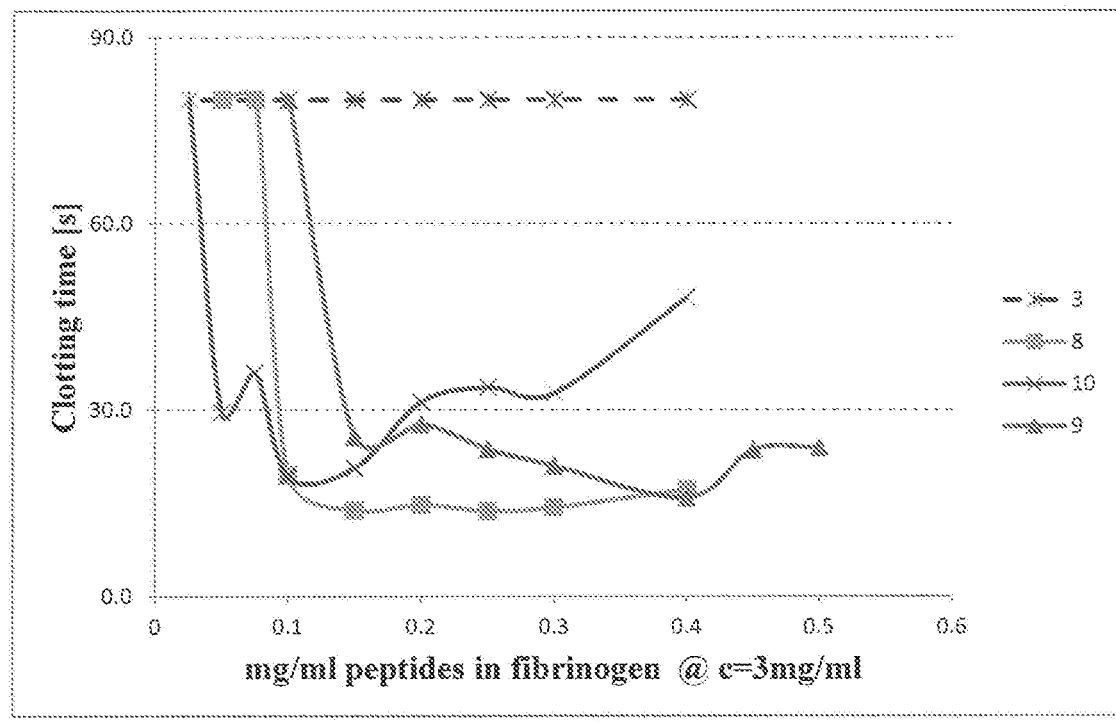
FIG. 3 shows the ability of several different peptide dendrimers to polymerise fibrinogen at varying concentrations. The numbering refers to the identity of the peptide dendrimer.

The ability of the dendrimers to copolymerise with fibrinogen was assessed using the same method described in Example 2, for a concentration of each dendrimer ranging from 0.005-0.5 mg/ml. FIG. 3 shows a plot of the clotting times (in seconds) obtained with increasing concentration of each different dendrimer.

The results show that changing the orientation of one of the fibrinogen-binding peptides of a three-branch dendrimer, so that the peptide is orientated with its amino-terminal end attached to the branched core (i.e. Dendrimer No. 3), reduced the ability of the dendrimer to copolymerise with fibrinogen (compare the clotting time of Dendrimer No. 3 with that of Dendrimer No. 10). However, at higher fibrinogen concentrations, Dendrimer No. 3 was able to copolymerise with fibrinogen (data not shown).

A three-branch dendrimer with a fibrinogen-binding peptide of different sequence orientated with its amino-terminal end attached to the branched core was able to copolymerise with fibrinogen (see the results for Dendrimer No. 8).

A three-branch dendrimer in which two of the fibrinogen-binding peptides comprise sequence that binds preferentially to hole 'b' in fibrinogen (sequence GPRPFPA (SEQ ID NO: 3)), with these peptides orientated with their carboxy-terminal end attached to the branched core, and the other peptide comprising the reverse sequence (i.e. sequence APFPRPG (SEQ ID NO: 14)) orientated with its amino-terminal end attached to the branched core (Dendrimer No. 9) was also very active in copolymerising with fibrinogen.

EXAMPLE 5

Ability of Peptide Dendrimers with Different Fibrinogen-Binding Peptide Sequences to Copolymerise with Fibrinogen The GPRPG (SEQ ID NO: 15) and GPRPFPA (SEQ ID NO: 3) motifs primarily bind to the 'a' hole on fibrinogen. This example describes an assessment of the ability of a chimeric peptide dendrimer (i.e. a peptide dendrimer with different fibrinogen-binding peptide sequences attached to the same branched core) to copolymerise with fibrinogen.

Peptide dendrimer No. 13 is a chimeric four-branch peptide dendrimer comprising two fibrinogen-binding peptides with sequence GPRPG- (SEQ ID NO: 15) (which has a binding preference for the 'a' hole), and two fibrinogen-binding peptides with sequence GHRPY-(SEQ ID NO: 11) (which binds preferentially to the 'b' hole). Non-chimeric peptide dendrimers Nos. 11 and 12 are four- and five-arm peptide dendrimers, respectively. Each fibrinogen-binding peptide of these dendrimers has the sequence GPRPG- (SEQ ID NO: 15). Each fibrinogen-binding peptide of Dendrimers Nos. 11, 12, and 13 is attached at its carboxy-terminal end to the branched core.

Figure 4:
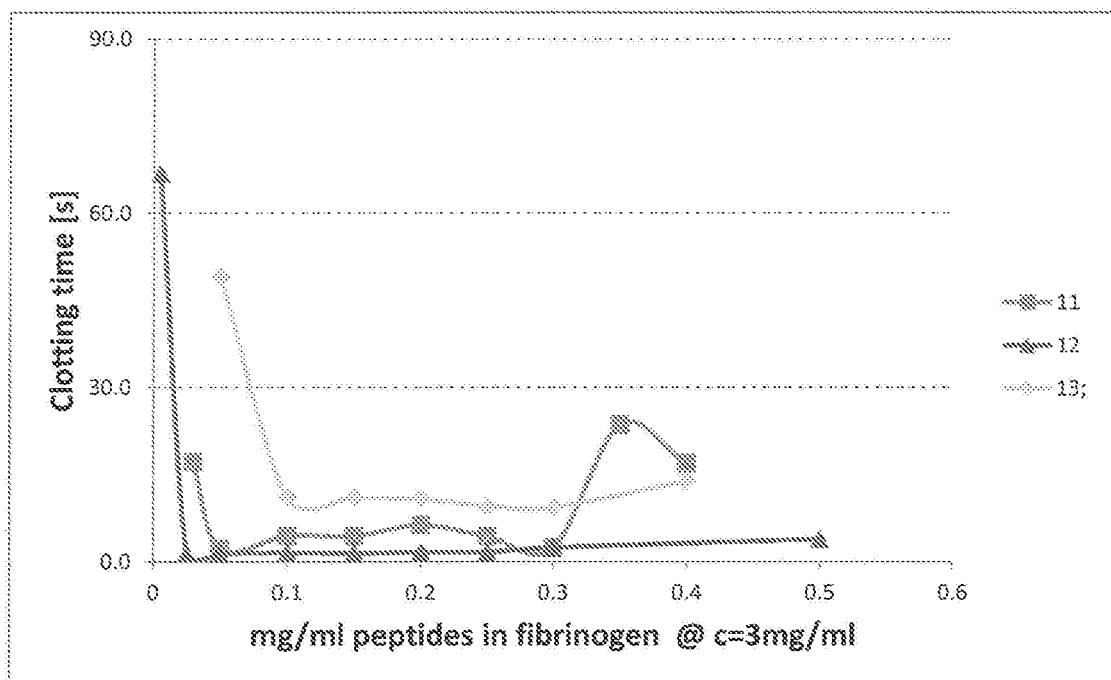
FIG. 4 shows the ability of several different peptide dendrimers to polymerise fibrinogen at varying concentrations. The numbering refers to the identity of the peptide dendrimer.

The ability of the dendrimers to copolymerise with fibrinogen was assessed using the same method described in Example 2, for a concentration of each dendrimer ranging from 0.005-0.5 mg/ml. FIG. 4 shows a plot of the clotting times (in seconds) obtained with increasing concentration of each different dendrimer.

Figure 5:
FIG. 5 shows a photograph of hydrogels formed by polymerisation of fibrinogen using different peptide dendrimers of the invention.

The results show that the clotting speed using the chimeric dendrimer was slower than the non-chimeric dendrimers at concentrations below 0.3 mg/ml. However, FIG. 5 shows a photograph of the hydrogels obtained using the different dendrimers. The gels are labelled with the number of the peptide dendrimer used (11, 12, and 13), and "P" labels a hydrogel formed using a product in which several fibrinogen-binding peptides are attached to soluble human serum albumin. The hydrogel formed by the chimeric dendrimer was more dense and contained less fluid compared to the hydrogels formed using dendrimers Nos. 11 and 12 (at 3 mg/ml fibrinogen, or at higher concentrations of fibrinogen). Thus, although the clotting time was slower using the chimeric dendrimer, the hydrogel formed using this dendrimer was more dense.

EXAMPLE 6

Ability of Mixtures of Peptide Dendrimers and Peptide Conjugates to Copolymerise with Fibrinogen Fibrinogen-binding peptide of sequence GPRP- (SEQ ID NO: 1) binds strongly and preferentially to the 'a' hole of fibrinogen (Laudano et al., 1978 PNAS 7S). Peptide Conjugate No. 1 comprises two fibrinogen-binding peptides with this sequence, each attached to a lysine residue. The first peptide is attached its carboxy-terminal end by a linker to the lysine residue, and the second peptide is attached at its amino-terminal end by a linker to the lysine residue. The carboxy-terminal end of the second peptide comprises an amide group.

Fibrinogen-binding peptide of sequence GHRPY- (SEQ ID NO: 11) binds strongly and preferentially to the 'b' hole of fibrinogen (Doolittle and Pandi, Biochemistry 2006, 45, 2657-2667). Peptide Conjugate No. 2 comprises a first fibrinogen-binding peptide with this sequence, attached at its carboxy-terminal end by a linker to a lysine residue. A second fibrinogen-binding peptide, which has the reverse sequence (YPRHG (SEQ ID NO: 16)), is attached at its amino terminal end by a linker to the lysine residue. The carboxy-terminal end of the second peptide comprises an amide group.

The linker allows the peptides to extend away from each other.

Figure 6:
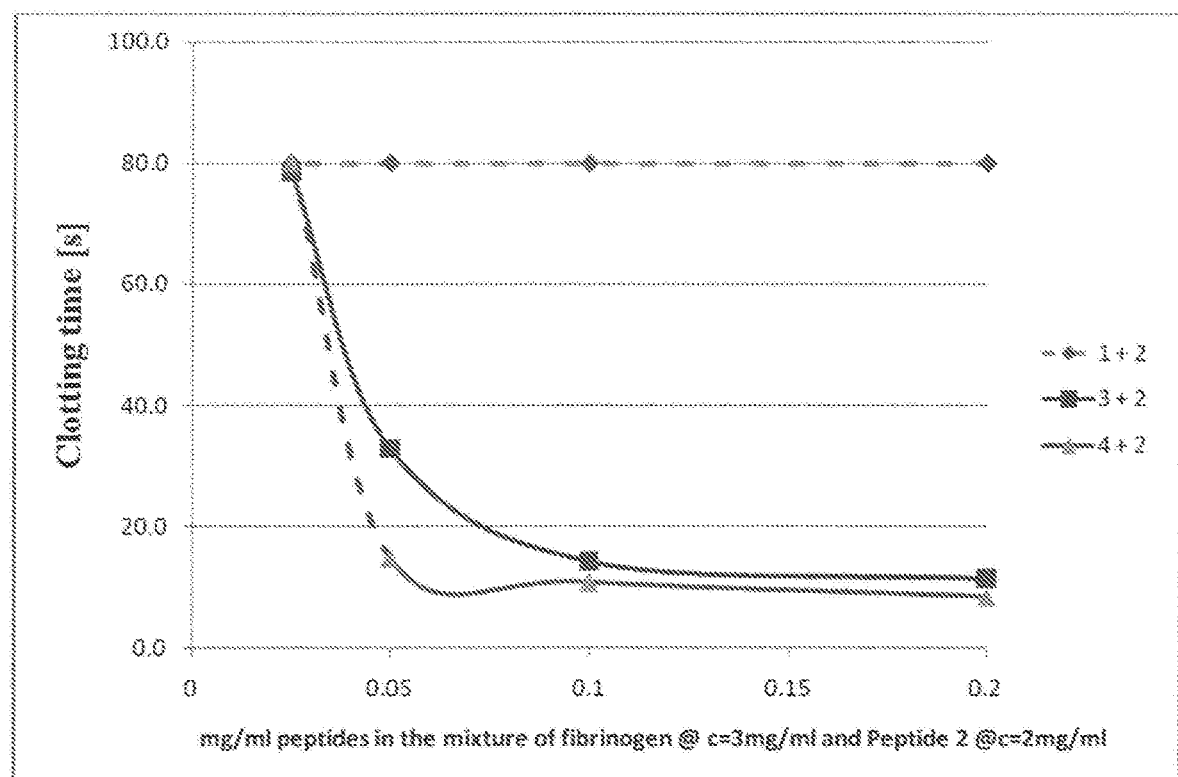
FIG. 6 shows the ability of different combinations of peptide dendrimers of the invention with peptide conjugates to polymerise fibrinogen at varying concentrations.

Peptide Conjugate No. 1 or 2 (2 mg/ml) was mixed with Peptide Dendrimer No. 3 or 4, and fibrinogen, and the ability of the mixtures to copolymerise with fibrinogen was assessed using the same method described in Example 2, for a concentration of each dendrimer ranging from 0.025-0.5 mg/ml. FIG. 6 shows a plot of the clotting times (in seconds) obtained with increasing concentration of each different dendrimer.

The results show that, surprisingly, only mixtures containing Peptide Conjugate No. 2 (i.e. with the B-knob peptides) and the dendrimer peptides were synergistic and increased activity, whereas mixtures containing the Peptide Conjugate No. 1 (the A-knob peptides) were not active when added to either Peptide Conjugate No. 2 or the peptide dendrimers.

EXAMPLE 7

Ability of Peptide Dendrimers to Polymerise Fibrinogen in Human Plasma

The ability of several different peptide dendrimers (Nos. 4, 5, 8, 9, 10, 11, 12, 13) to polymerise fibrinogen in human plasma was tested.

30 μL of each dendrimer (at a concentration of 0.25 mg/ml) was added to 100 μL human plasma at 37° C., and polymerisation of fibrinogen was determined using a Sigma Amelung KC4 Delta coagulation analyzer.

Figure 7:
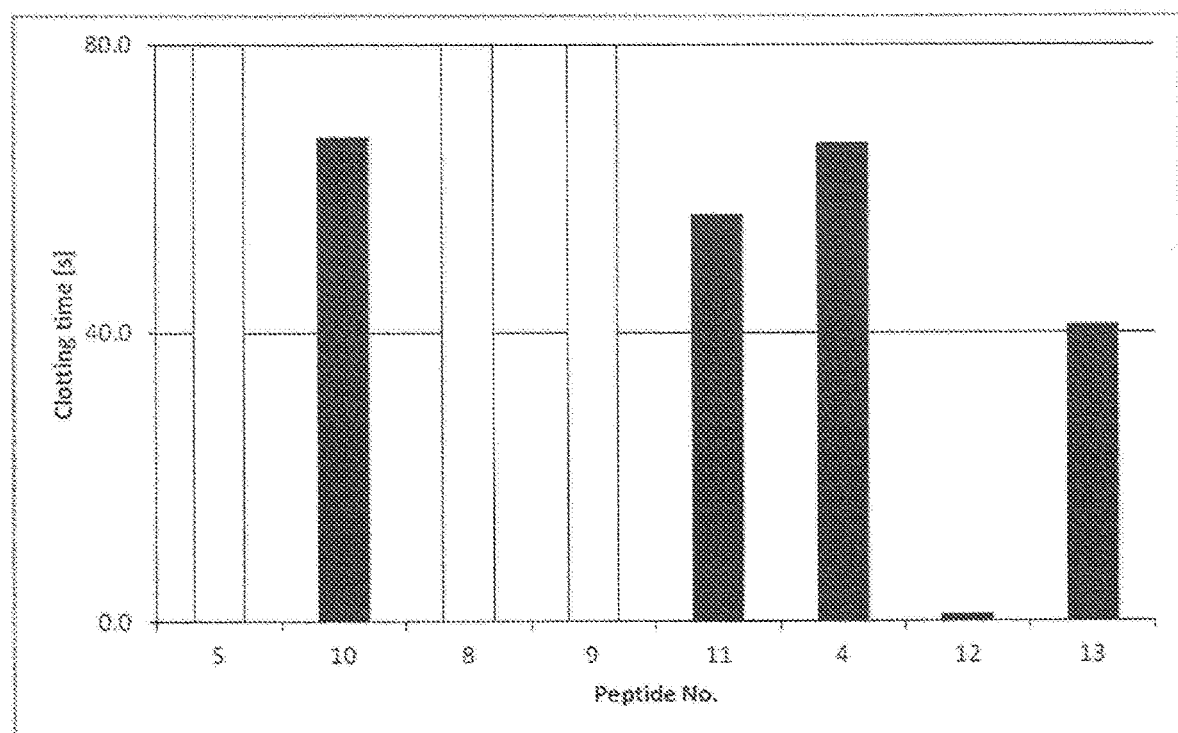
FIG. 7 shows the ability of several different peptide dendrimers of the invention to polymerise fibrinogen in human plasma.

The clotting times for each dendrimer are shown in FIG. 7, and show that peptide dendrimers Nos. 10, 11, 4, 12 and 13 were able to polymerise fibrinogen in human plasma, with dendrimer No. 12 being particularly effective (with a clotting time of less than one second). However, peptide dendrimers Nos. 5, 8, and 9 were not able to polymerise fibrinogen in human plasma.

EXAMPLE 8

Effect of Sterilisation on Ready-to-Use Peptide Dendrimer Formulations

This example describes the effect of Gamma irradiation on the haemostatic activity of peptide dendrimers formulated as a ready-to-use paste with hydrated gelatin.

2 ml of solution of Peptide Dendrimer No. 12 or 13 was mixed with SURGIFLO Haemostatic Matrix (a hydrated flowable gelatin matrix) to form a paste of each peptide. Each paste was sterilised by irradiation with $^{60}$Co gamma rays at a dose of 30 kGy, and then stored at room temperature. Samples of the sterilised pastes were used for testing after storage for two and four weeks.

After storage, peptide dendrimers were extracted from each paste using 10 mM HEPES buffer. 30 μL of each extract (with a peptide concentration of about 0.25 mg/ml) was added to 100 μL of human fibrinogen at 3 mg/ml, and the ability of each dendrimer to polymerise fibrinogen (the 'clotting' activity) at 37° C. was determined using a Sigma Amelung KC4 Delta coagulation analyser. The polymerisation activity of non-irradiated control samples was also determined. The results are summarized in the Table below.

| | Clotting activity (seconds) | | |
| --- | --- | --- | --- |
| Peptide dendrimer no. | Non-irradiated control | Storage for 2 weeks post irradiation | Storage for 4 weeks post irradiation |
| 12 | 1 | 1 | 1 |
| 13 | 4.3 | 9.4 | 10 |

The results show that peptide dendrimers of the invention, formulated as a ready-to-use paste with hydrated gelatin, retain ability to polymerise fibrinogen after sterilization by irradiation.

SEQUENCE LISTING

```
<160> NUMBER OF SEQ ID NOS: 16

<210> SEQ ID NO 1
<211> LENGTH: 4
<212> TYPE: PRT
<213> ORGANISM: Homo sapiens

<400> SEQUENCE: 1

Gly Pro Arg Pro
1

<210> SEQ ID NO 2
<211> LENGTH: 4
<212> TYPE: PRT
<213> ORGANISM: Homo sapiens

<400> SEQUENCE: 2

Gly Pro Arg Val
1

<210> SEQ ID NO 3
<211> LENGTH: 7
<212> TYPE: PRT
<213> ORGANISM: Homo sapiens

<400> SEQUENCE: 3
```

```
Gly Pro Arg Pro Phe Pro Ala
1               5

<210> SEQ ID NO 4
<211> LENGTH: 7
<212> TYPE: PRT
<213> ORGANISM: Homo sapiens

<400> SEQUENCE: 4

Gly Pro Arg Val Val Ala Ala
1               5

<210> SEQ ID NO 5
<211> LENGTH: 8
<212> TYPE: PRT
<213> ORGANISM: Homo sapiens

<400> SEQUENCE: 5

Gly Pro Arg Pro Val Val Glu Arg
1               5

<210> SEQ ID NO 6
<211> LENGTH: 6
<212> TYPE: PRT
<213> ORGANISM: Homo sapiens

<400> SEQUENCE: 6

Gly Pro Arg Pro Ala Ala
1               5

<210> SEQ ID NO 7
<211> LENGTH: 7
<212> TYPE: PRT
<213> ORGANISM: Homo sapiens

<400> SEQUENCE: 7

Gly Pro Arg Pro Pro Glu Cys
1               5

<210> SEQ ID NO 8
<211> LENGTH: 7
<212> TYPE: PRT
<213> ORGANISM: Homo sapiens

<400> SEQUENCE: 8

Gly Pro Arg Pro Pro Glu Arg
1               5

<210> SEQ ID NO 9
<211> LENGTH: 6
<212> TYPE: PRT
<213> ORGANISM: Homo sapiens

<400> SEQUENCE: 9

Gly Pro Ser Pro Ala Ala
1               5

<210> SEQ ID NO 10
<211> LENGTH: 4
<212> TYPE: PRT
<213> ORGANISM: Homo sapiens

<400> SEQUENCE: 10

Gly His Arg Pro
1
```

<210> SEQ ID NO 11
<211> LENGTH: 5
<212> TYPE: PRT
<213> ORGANISM: Homo sapiens

<400> SEQUENCE: 11

Gly His Arg Pro Tyr
1               5

<210> SEQ ID NO 12
<211> LENGTH: 5
<212> TYPE: PRT
<213> ORGANISM: Homo sapiens

<400> SEQUENCE: 12

Gly His Arg Pro Leu
1               5

<210> SEQ ID NO 13
<211> LENGTH: 5
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Carboxy-terminal end comprises an amide group

<400> SEQUENCE: 13

Gly His Arg Pro Tyr
1               5

<210> SEQ ID NO 14
<211> LENGTH: 7
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Carboxy-terminal end may comprise an amide
      group

<400> SEQUENCE: 14

Ala Pro Phe Pro Arg Pro Gly
1               5

<210> SEQ ID NO 15
<211> LENGTH: 5
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Carbox-terminal end may comprise an amide group

<400> SEQUENCE: 15

Gly Pro Arg Pro Gly
1               5

<210> SEQ ID NO 16
<211> LENGTH: 5
<212> TYPE: PRT
<213> ORGANISM: Homo sapiens

```
<220> FEATURE:
<221> NAME/KEY: misc_feature
<222> LOCATION: (5)..(5)
<223> OTHER INFORMATION: Carboxy-terminal end comprises an amide group

<400> SEQUENCE: 16

Tyr Pro Arg His Gly
1               5
```

And insert in its place the following compound:
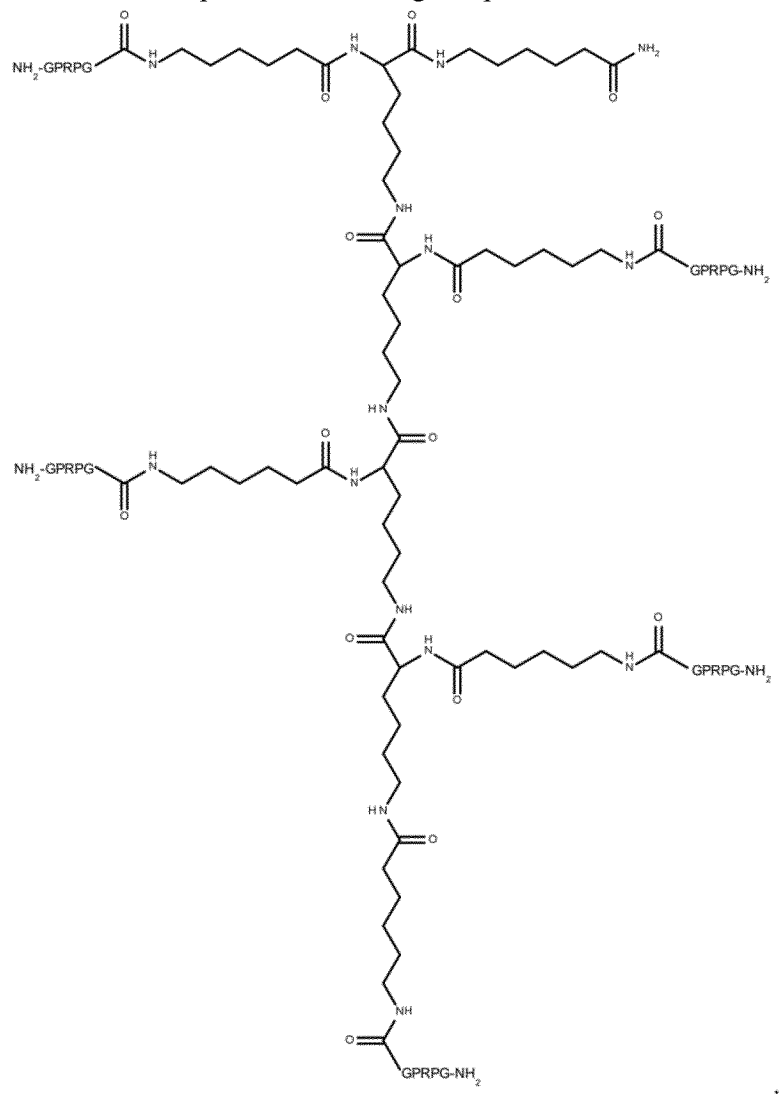

The invention claimed is:

1. A peptide dendrimer that comprises a branched core, and a plurality of fibrinogen-binding peptides separately covalently attached to the branched core by a non-peptide linker, wherein the peptide dendrimer comprises the structure of Formula (I):

$$\text{FBP-(linker)-X-(linker)-Y} \atop | \atop Z \qquad (I)$$

where:
FBP is a fibrinogen-binding peptide;
-(linker)- is a non-peptide linker comprising —NH(CH$_2$)$_n$CO—, where n is 1-10;
X is a tri-functional amino acid residue;
Y is -FBP or —NH$_2$; and
Z is -[—X-(linker)-FBP]$_a$-(linker)-FBP, where a is 1-10.

2. The peptide dendrimer according to claim 1, wherein the tri-functional amino acid residues of Formula (I) comprise a lysine, ornithine, arginine, aspartic acid, glutamic acid, asparagine, glutamine, or cysteine residue.

3. The peptide dendrimer according to claim 1, wherein the fibrinogen-binding peptides bind preferentially to hole 'a' of fibrinogen over hole 'b' of fibrinogen.

4. The peptide dendrimer according to claim 1, wherein the fibrinogen-binding peptides bind preferentially to hole 'b' of fibrinogen over hole 'a' of fibrinogen.

5. The peptide dendrimer according to claim 1, which does not comprise the following:

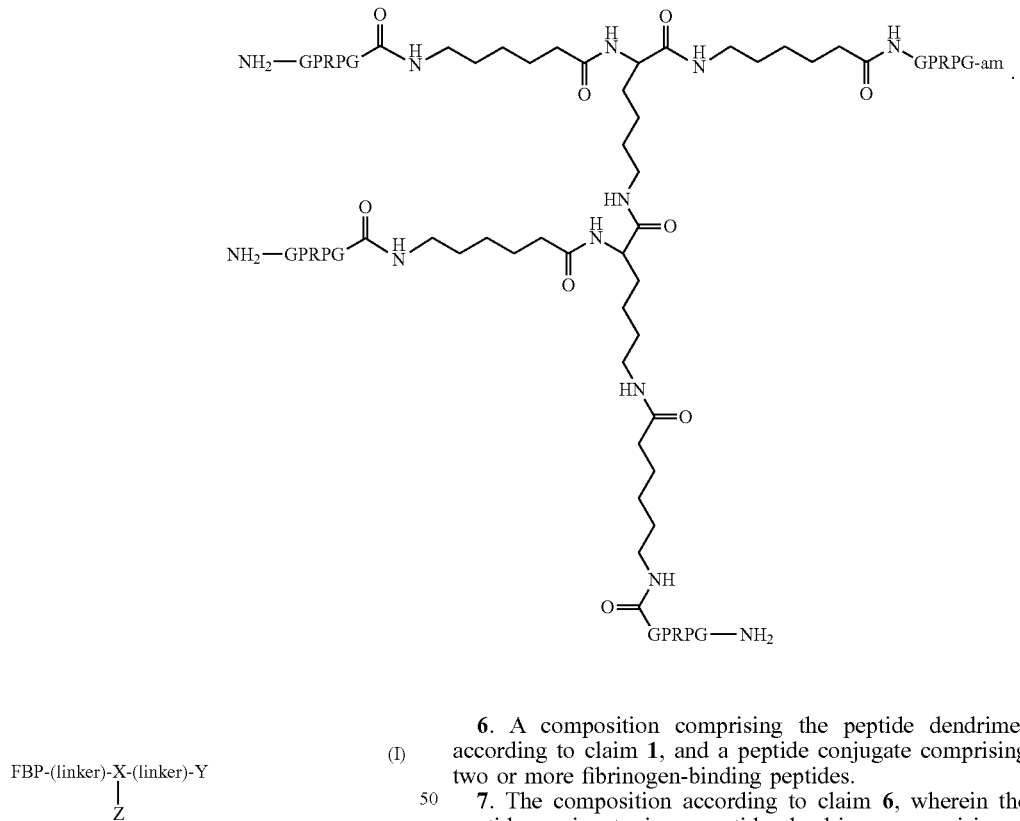

6. A composition comprising the peptide dendrimer according to claim 1, and a peptide conjugate comprising two or more fibrinogen-binding peptides.

7. The composition according to claim 6, wherein the peptide conjugate is a peptide dendrimer comprising a branched core and a plurality of fibrinogen-binding peptides separately covalently attached to the branched core by a non-peptide linker, wherein the branched core of said peptide dendrimer comprises:

from two to ten multi-functional amino acid residues, wherein each fibrinogen-binding peptide is separately covalently attached, via a non-peptide linker, to a multi-functional amino acid residue of the branched core;

a plurality of multi-functional amino acid residues, wherein one or more fibrinogen-binding peptides are separately covalently attached, via a non-peptide linker, to each of at least two adjacent multi-functional amino acid residues of the branched core;

a plurality of multi-functional amino acid residues, wherein two or more fibrinogen-binding peptides are separately covalently attached, via a non-peptide linker, to at least one of the multi-functional amino acid residues of the branched core;
a plurality of multi-functional amino acid residues, wherein two or more multi-functional amino acid residues are covalently linked through a side chain of an adjacent multi-functional amino acid residue; or
a single multi-functional amino acid residue, and a fibrinogen-binding peptide is separately covalently attached, via a non-peptide linker, to each functional group of the multi-functional amino acid residue;
wherein the multi-functional amino acid residues comprise tri- or tetra-functional amino acid residues, or tri- and tetra-functional amino acid residues, or the single multi-functional amino acid residue is a tri- or tetra-functional amino acid residue.

8. A pharmaceutical composition, which comprises the peptide dendrimer according to claim 1, and a pharmaceutically acceptable carrier, excipient, or diluent.

9. The pharmaceutical composition according to claim 8, which is a ready-to-use haemostatic formulation in which the pharmaceutically acceptable carrier, excipient, or diluent comprises hydrated gelatin.

10. The peptide dendrimer according to claim 1, which is sterile.

11. A method of sterilising the peptide dendrimer according to claim 1, which comprises: exposing the peptide dendrimer to gamma irradiation.

12. A method of polymerising fibrinogen, which comprises: contacting fibrinogen with the peptide dendrimer according to claim 1.

13. A kit for formation of a hydrogel, which comprises the peptide dendrimer according to claim 1 and, separately, fibrinogen.

14. A hydrogel comprising a copolymer of the peptide dendrimer according to claim 1, and fibrinogen.

15. A method of treating bleeding, or of treating a wound, which comprises: administering the peptide dendrimer according to claim 1 to a site of bleeding or to a wound.

16. A method according to claim 15, which comprises administering fibrinogen and the peptide dendrimer to the site of bleeding or to the wound.

17. A pharmaceutical composition, which comprises the composition according to claim 6 and a pharmaceutically acceptable carrier, excipient, or diluent.

18. The composition of claim 6, which is sterile.

19. A method of sterilising the composition of claim 6 comprising: exposing the composition to gamma irradiation.

20. A method of polymerising fibrinogen, which comprises: contacting fibrinogen with the composition of claim 6.

21. A kit for formation of a hydrogel comprising: the composition of claim 6 and, separately, fibrinogen.

22. A hydrogel comprising a copolymer of the composition of claim 6 and fibrinogen.

23. A method of treating bleeding, or of treating a wound, which comprises: administering the composition of claim 6 to a site of bleeding or to a wound.

24. The peptide dendrimer of claim 1, wherein said dendrimer comprises:

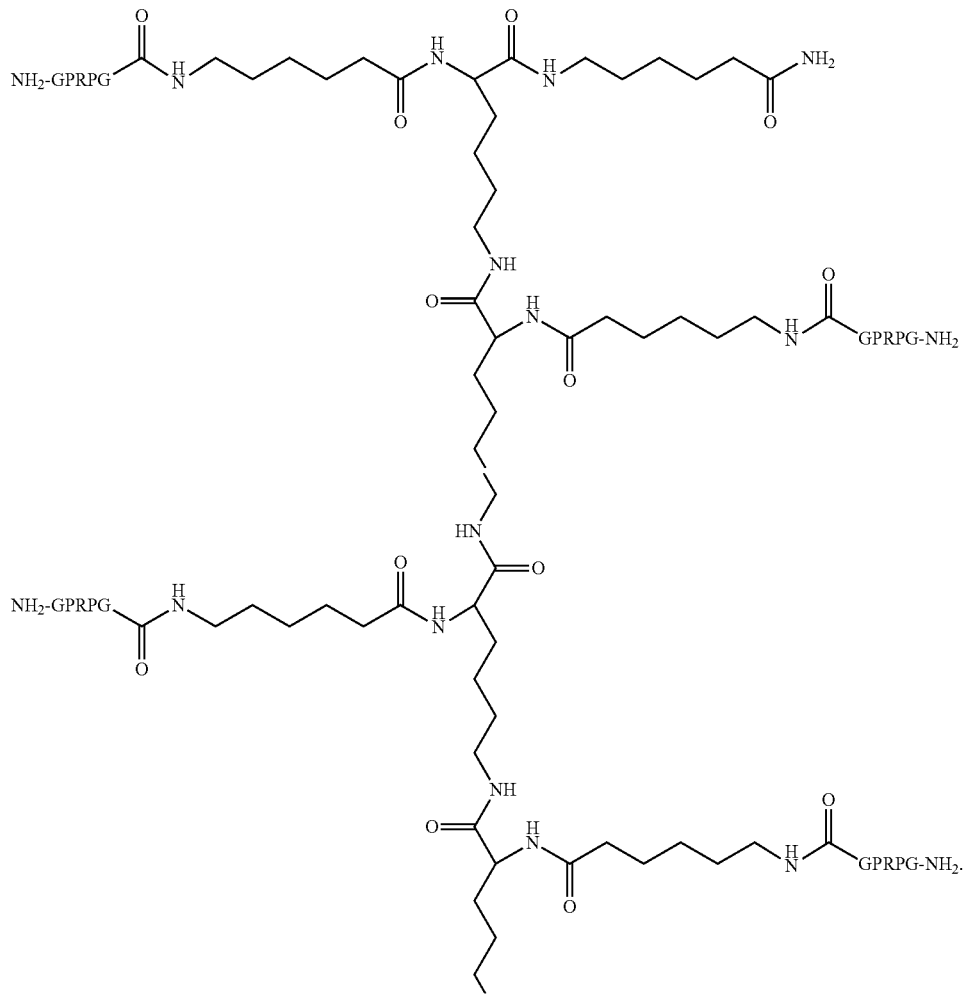

-continued
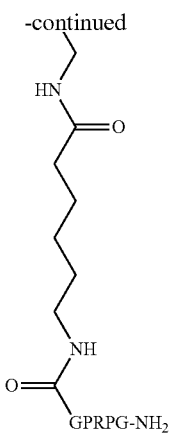
25. The peptide dendrimer according to claim 1, wherein the tri-functional amino acid residues of Formula (I) are lysine residues.
* * * * *

UNITED STATES PATENT AND TRADEMARK OFFICE
CERTIFICATE OF CORRECTION

Page 1 of 2

PATENT NO. : 10,994,047 B2
APPLICATION NO. : 15/110630
DATED : May 4, 2021
INVENTOR(S) : Renata Zbozien It is certified that error appears in the above-identified patent and that said Letters Patent is hereby corrected as shown below:

In the Claims

In Claim 24, Column 42, Lines 29-67 and Column 43, Lines 1-19, please delete the following compounds:

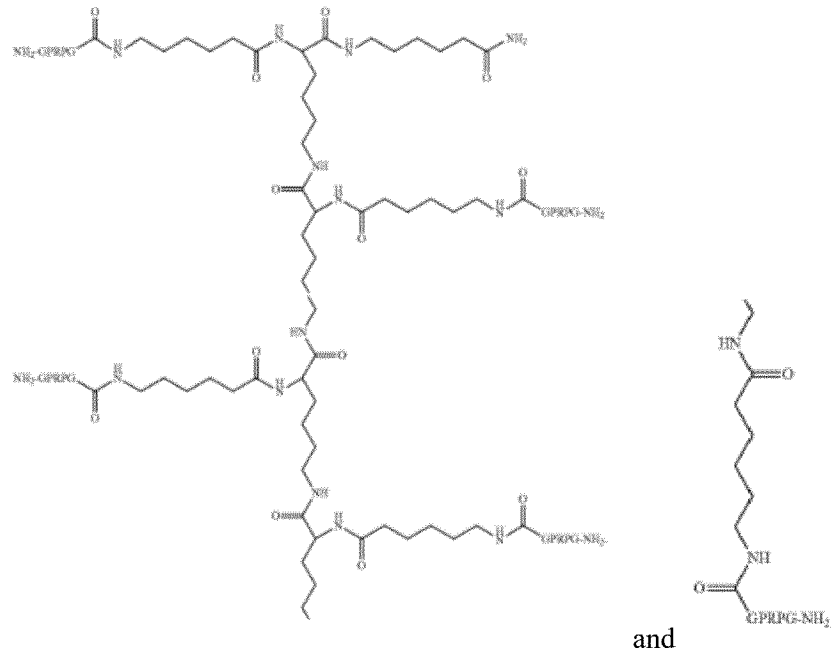

and

Signed and Sealed this
Seventeenth Day of August, 2021

Drew Hirshfeld
*Performing the Functions and Duties of the
Under Secretary of Commerce for Intellectual Property and
Director of the United States Patent and Trademark Office*